United States Patent [19]
Tai et al.

[11] Patent Number: 5,665,875
[45] Date of Patent: Sep. 9, 1997

[54] WATER-SOLUBLE TETRAAZAPORPHINS AND FLUOROCHROME FOR LABELING

[75] Inventors: Seiji Tai; Mitsuo Katayose; Hiroo Watanabe, all of Hitachi, Japan

[73] Assignee: Hitachi Chemical Co., Ltd., Tokyo, Japan

[21] Appl. No.: 460,930

[22] Filed: Jun. 5, 1995

Related U.S. Application Data

[62] Division of Ser. No. 145,199, Nov. 3, 1993.

[30] Foreign Application Priority Data

Nov. 10, 1992 [JP] Japan ............................. 4-299773
Aug. 25, 1993 [JP] Japan ............................. 5-210059

[51] Int. Cl.[6] .......................... C09B 47/00; C07F 7/08
[52] U.S. Cl. ...................... 536/26.6; 540/121; 540/139; 540/140; 436/56
[58] Field of Search ..................... 540/121, 139, 540/140; 436/56; 536/26.6

[56] References Cited

FOREIGN PATENT DOCUMENTS 0502723  9/1992  European Pat. Off. .

*Primary Examiner*—Scott W. Houtteman
*Attorney, Agent, or Firm*—Antonelli, Terry, Stout & Kraus, LLP

[57] ABSTRACT

Tetraazaporphins represented by the general formula (I):

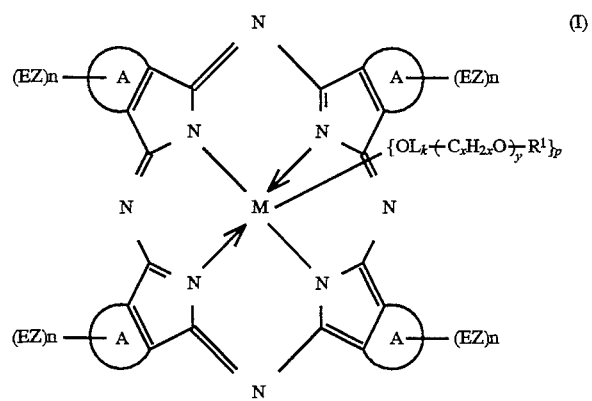

provide substances derived from organisms (e.g. antigens, antibodies, nucleotides, etc.) which have been labeled with a fluorochrome for labeling comprising the tetraazaporphin; reagents comprising any of the labeled substances which can be utilized for assay of various antigens, drugs, DNAs and the like; and analysis of the base sequence of DNA. Fluorescence analysis can be carried out using the labeled substances.

12 Claims, 21 Drawing Sheets

WATER-SOLUBLE TETRAAZAPORPHINS AND FLUOROCHROME FOR LABELING

This application is a divisional application of application Ser. No. 08/145,199, filed Nov. 3, 1993.

BACKGROUND OF THE INVENTION

This invention relates to a water-soluble tetraazaporphin, a fluorochrome for labeling, a substance derived from an organism which has been labeled with the fluorochrome for labeling, a reagent comprising any of them, and a fluorescence analysis process using any of them.

Since early times, label methods have been utilized for investigation of various substances such as molecules, cells, antigens, antibodies, DNA, RNA, polypeptides, etc. A label method using a radioisotope (RI) has heretofore been widely utilized because it has been studied for a long period of time. Since RI entails a severe exposure hazard, employment of RI requires both a special license and a special laboratory, and has been possible only for specified persons in specified facilities.

On the other hand, a method using a coloring substance, chemiluminescence method, fluorescence method, etc. are noted as label methods free from danger because they need not use RI. The method using a coloring substance cannot have a high detection sensitivity and hence is not so useful as to replace the RI method thereby. On the other hand, the chemiluminescence method and the fluorescence method are considered safe label methods which can replace the RI method, because their detection sensitivity can be enhanced. However, in the chemiluminescence method, luminescence is caused by combination of two or more chemical reactions, so that a complicated procedure is required. Therefore, fluorescence label method is the most excellent label method from the viewpoint Of safety, simplicity and high sensitivity.

There have been known only dyes which emit fluorescence in the ultraviolet region, but Rhodamine dyes and oxazine dyes have recently come to be known to the art as dyes which can be excited by means of an argon laser or a He—Ne laser.

As a light source, a compact semiconductor laser (670 to 840 nm) has recently become available at a low price. It is likely to become a leading light source because of the demand for an inexpensive, small and light instrument. However, there is a problem in that conventional Rhodamine dyes, oxazine dyes and the like cannot be used when the semiconductor laser is used.

It has recently been proposed that phthalocyanine capable of showing a proper fluorescence quantum yield and a high water-solubility is used as a fluorochrome for labeling (International Publication Nos. WO 88/04777 and WO 90/02747). However, the absorption maximum wavelength region and fluorescence emission wavelength region in Q-band of phthalocyanine derivatives are in a range of 670 to 690 nm, so that the phthalocyanine derivatives cannot be excited by means of a semiconductor laser emitting a wavelength of 700 nm or more. Moreover, when a semiconductor laser emitting a wavelength of 670 to 680 nm is used, its emitting wavelength region and the fluorescence emission wavelength region-overlap each other, so that it is impossible to judge whether light detected is derived from fluorescent radiation emitted or laser beam scattered. Therefore, the phthalocyanine derivatives cannot be utilized. In short, the phthalocyanine derivatives have a fatal defect in that they cannot be used at all in a system using a semiconductor laser which is a leading system.

Furthermore, in a system in which a substance in a living body, for example, a heme in blood is present together with an analyte to be measured, measurement of the analyte is restricted by the substance in the living body because the heme has an absorption wavelength region of 700 nm or less which overlaps with that of phthalocyanine.

SUMMARY OF THE INVENTION

This invention provides a novel compound, a fluorochrome for labeling, a reagent, a reagent for clinical examination, and a fluorescence analysis process which are not affected by substances in a living body, such as hemes present in blood, can be used for measurement by means of an inexpensive and compact semiconductor laser (670 to 840 nm), and are useful for assay of various antigens, drugs, DNA's, etc. and analysis of the base sequence of DNA.

This invention provides the following items (1) to (12).

(1) A water-soluble tetraazaporphin represented by the general formula (I):

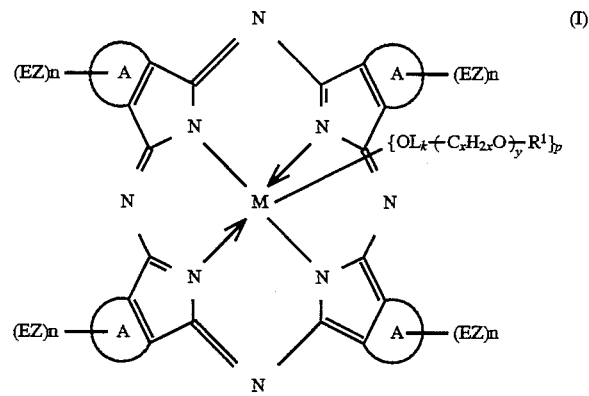

wherein M is Al, Si, P, Ga, Ge or Sc; k is zero or an integer of 1; in the case of k being 1, L is —Si(CH$_3$)$_2$(CH$_2$)$_a$NH—,
—Si(CH$_3$)$_2$(CH$_2$)$_b$NH.COO—,
—Si(CH$_3$)$_2$O— or
—Si(CH$_3$)$_2$NH— wherein a and b are independently an integer of 1 to 6; x is an integer of i to 6; y is an integer of 1 to 200; R$^1$ is a hydrogen atom, a linear, branched or cyclic alkyl group, an aryl group, a heterocyclic group or an aralkyl group; p is an integer of 1 or 2 indicating the number of groups represented by the formula —OL$_K$—(C$_x$H$_{2x}$O)$_y$—R$^1$ which are bonded to M; four A's, which may be the same or different, are independently a fused polycyclic aromatic ring formed from two or more aromatic rings, which may have substituents XQ's or Q's in a number of m (X is an oxygen atom, a sulfur atom, a nitrogen atom, a phosphorus atom, a silicon atom, a selenium atom, NH.CO, NH.PO$_2$, NH.SO$_2$, O.CO, O.SO$_2$, O.PO$_2$, S.CO, S.SO$_2$, S.PO$_2$, CO, SO$_2$ or PO$_2$; Q is a saturated or unsaturated hydrocarbon group or a heterocyclic group; and each m is the same or different and independently an integer of 1 to 4; each n is the same or different and independently zero or an integer of 1 or more, 4n (the sum of four n's, namely, the total number of EZ's) being an integer of 1 or more; each substituent (EZ) in a number of n is the same or different and independently bonded to the fused polycyclic aromatic ring A and/or Q; and E is a cationic group in the case of Z being an anion, E is an anionic group in the case of Z being a cation, and E is a bonded group containing a polyethylene glycol residue, a polyether residue, a polyamine residue, a polyalcohol residue or a polycarboxylic acid residue in the case of z being absent.

(2) A fluorochrome for labeling comprising the water-soluble tetraazaporphin of the above item (1).

(3) A reagent comprising the fluorochrome for labeling of the above item (2).

(4) A reagent comprising the fluorochrome for labeling of the above item (2) and a nonionic surfactant.

(5) A substance derived from an organism which has been labeled with the fluorochrome for labeling of the above item (2).

(6) A reagent comprising the labeled substance derived from an organism of the above item (5).

(7) A reagent comprising the labeled substance derived from an organism of the above item (5) and a non-ionic surfactant.

(8) A substance derived from an organism according to the above item (5) or a reagent according to the above item (6) or (7), wherein the substance derived from an organism is an antigen, an antibody or a nucleotide.

(9) A substance derived from an organism or a reagent according to the above item (8), wherein the antigen is a drug.

(10) A substance derived from an organism or a reagent according to the above item (8), wherein the antibody is a monoclonal antibody.

(11) A substance derived from an organism or a reagent according to the above item (8), wherein the nucleotide is an oligonucleotide or a polynucleotide.

(12) A substance derived from an organism or a reagent according to the above item (8), wherein the nucleotide is ATP, CTP, GTP, TTP, UTP, dATP, dCTP, dGTP, dTTP, dUTP, ddATP, ddCTP, ddGTP, ddTTP, ddUTP, or a derivative thereof.

(13) A fluorescence analysis process characterized by using the fluorochrome for labeling of the above item (2) as a fluorescent label.

(14) A fluorescence analysis process according to the above item (13), which uses a semiconductor laser emitting a wavelength of 670 to 840 nmas a light source.

(15) A fluorescence analysis process according to the above item (13) or (14), which uses the labeled substance derived from an organism of the above item (5).

DESCRIPTION OF THE PREFERRED EMBODIMENTS

Figure 1:
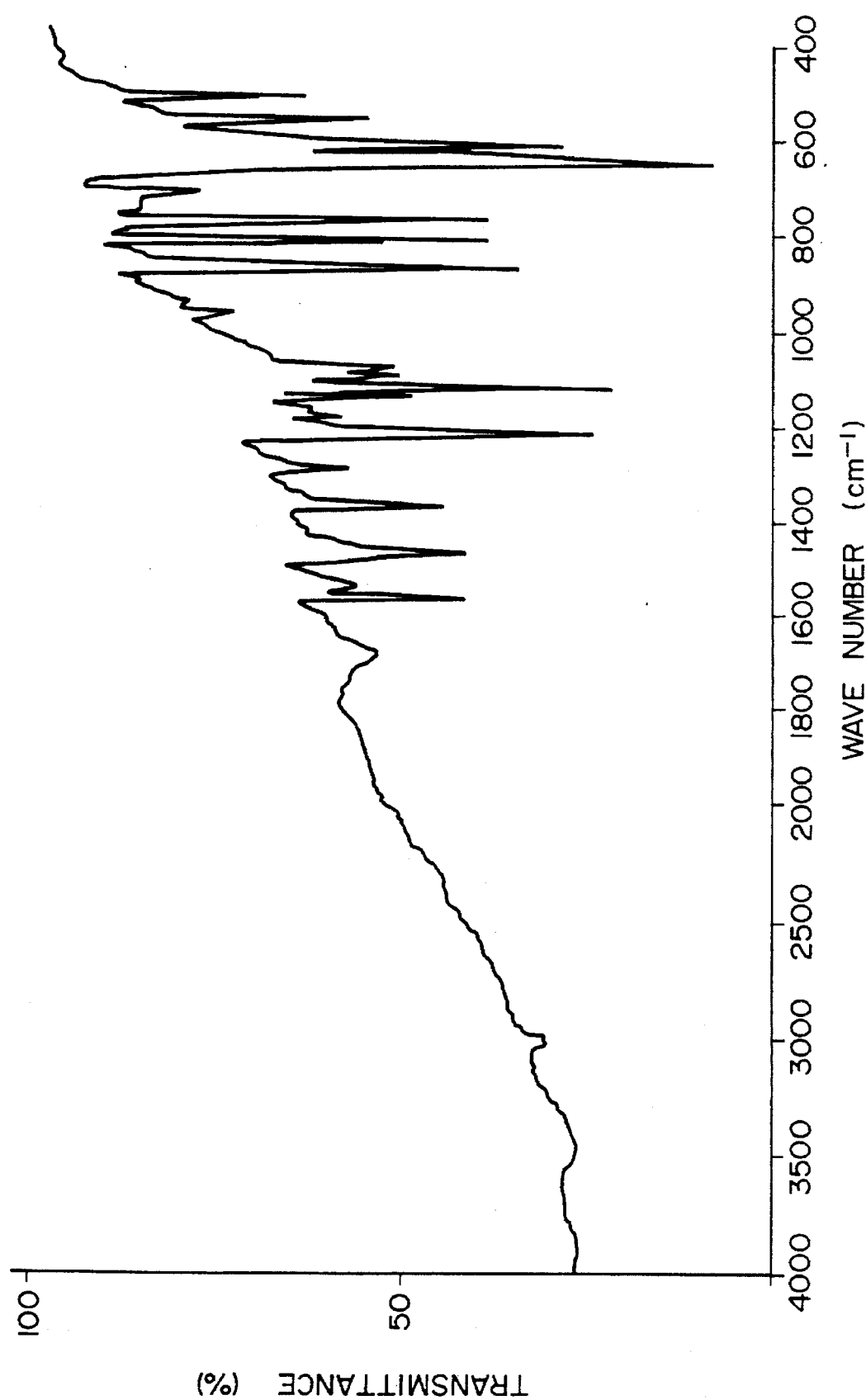
FIG. 1 is an IR spectrum (neat) of 3,4-bis(dibromomethyl) bromobenzene.

The water-soluble tetraazaporphin derivative of the present invention is represented by the formula:

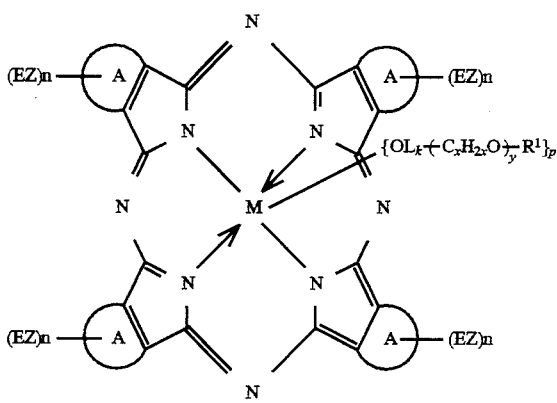 (I)

and since it is highly soluble not only in water but also in polar organic solvents such as methanol, ethanol, etc., it can easily be purified to be improved in purity, by chromatography, recrystallization, reprecipitation, etc.

In the compound of the formula (I) of this invention, the linear, branched or cyclic alkyl group, aryl group, heterocyclic group or aralkyl group represented by $R^1$ include methyl group, ethyl group, propyl group, isopropyl group, butyl group, isobutyl group, sec-butyl group, tert-butyl group, pentyl group, sec-pentyl group, tert-pentyl group, neopentyl group, 2-ethylhexyl group, cyclopropyl group, cyclobutyl group, cyclopentyl group, cyclohexyl group, phenyl group, o-tolyl group, m-tolyl group, p-tolyl group, 2,3-xylyl group, 2,4-xylyl group, o-cumenyl group, m-cumenyl group, p-cumenyl group, mesityl group, thienyl group, furyl group, tetrahydrofurfuryl, benzyl group, phenethyl group, trityl group, naphthyl group, norbornyl group, etc.

The group represented by the formula —$(C_xH_{2x}O)y$— includes, for example, polyethylene glycol residues and polypropylene glycol residues, which have an average molecular weight of 200 to 10,000.

As to XQ or Q, i.e., the substituent which A may have in the general formula (I), specific examples of the saturated or unsaturated, linear, branched or cyclic hydrocarbon group represented by Q are methyl group, ethyl group, propyl group, isopropyl group, butyl group, isobutyl group, sec-butyl group, tert-butyl group, pentyl group, isopentyl group, neopentyl group, hexyl group, heptyl group, octyl group, nonyl group, decyl group, undecyl group, dodecyl group, vinyl group, 1-propenyl group, allyl group, isopropenyl group, 1-butenyl group, 2-butenyl group, 2-pentenyl group, ethynyl group, cyclopropyl group, cyclobutyl group, cyclopentyl group, cyclohexyl group, cyclohexenyl group, phenyl group, tolyl group, xylyl group, mesityl group, cumenyl group, benzyl group, phenethyl group, naphthyl group, etc. Specific examples of the heterocyclic group are furyl group, thienyl group, pyrrolyl group, etc.

The anion represented by Z includes $Cl^-$, $Br^-$, $I^-$, $ClO_4^-$, $SO_4^-$, $PO_3^-$, etc. The cation represented by Z includes $H^+$, $Li^+$, $Na^+$, $K^+$, $Mg^{2+}$, $Ca^{2+}$, ammonium ion, etc. The cationic group represented by E includes, for example, —$N^+R^2_3$ and

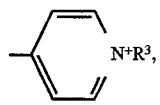

wherein $R^2$ and $R^3$ are independently an alkyl group, an aryl group, a heterocyclic group or an aralkyl group which are the same as those exemplified above for $R^1$ and may have one or more hydrophilic substituents. The anionic group represented by E includes —$COO^{13}$, —$OSO_3^-$, —$OPO_3^-$, —$SO_3^-$, etc. The fused polycyclic aromatic ring formed from two or more aromatic rings which is represented by A, includes naphthalene ring, anthracene ring, phenanthrene ring, quinoline ring, quinoxaline ring, chrysene ring, etc. The bonding position of the fused polycyclic aromatic ring has not any limitation.

The kind and form of the above substituents have a great influence not only on the solubility of the novel tetraazaporphin of the above general formula (I) in water or polar organic solvents but also on the absorption spectrum and the wavelength of absorption maximum, or the wavelength of fluorescence emission maximum and the fluorescence emission intensity, in a solution.

The symbol "p" represents zero or an integer of 1 or 2 indicating the number of groups of the formula —$OL_K$—$(C_xH_{2x}O)_y$—$R^1$ bonded to M. When M is Al, Sc or Ga, p is 1. When M is Si, P or Ge, p is 2.

In the compound of the general formula (I), the water-soluble group represented by EZ is bonded to the fused polycyclic aromatic ring represented by A and/or the hydrocarbon group or heterocyclic group for Q bonded to the aromatic ring. The position(s) to which EZ is bonded is determined by the synthetic pathway of the compound of the general formula (I). For example, when as shown in Example 2 described hereinafter, XQ having one or more substituents (ester groups) convertible into EZ by hydrolysis is introduced into the fused polycyclic aromatic ring represented by A and then hydrolyzed, the product has a water-soluble group(s) EZ as substituent(s) only in Q.

Specific examples of the water-soluble tetraazaporphin of this invention are shown in Table 1.

TABLE 1

| No. | M | A | L | k | $-(C_xH_{2x}O)_y-$ | $R^1$ | p | XQ or Q | m | EZ | 4n |
|---|---|---|---|---|---|---|---|---|---|---|---|
| 1 | Si | 2,3-Naphthalene ring | $-Si(CH_3)_2(CH_2)_3NH-$ | 1 | $-(C_2H_4O)_y-$ [MW ca. 2000] | $-CH_3$ | 2 | — | 0 | COONa | 4 |
| 2 | Si | 2,3-Naphthalene ring | $-Si(CH_3)_2(CH_2)_3NH-$ | 1 | $-(C_2H_4O)_y-$ [MW ca. 550] | $-CH_3$ | 2 | — | 0 | COONa | 4 |
| 3 | Si | 2,3-Naphthalene ring | $-Si(CH_3)_2(CH_2)_3NH-$ | 1 | $-(C_2H_4O)_y-$ [MW ca. 2000] | $-CH_3$ | 2 | —S—C6H5 | 1 | COONa | 8 |
| 4 | Si | 2,3-Naphthalene ring | $-Si(CH_3)_2(CH_2)_3NH-$ | 1 | $-(C_2H_4O)_y-$ [MW ca. 750] | $-CH_3$ | 2 | —S—C6H5 | 1 | COONa | 8 |
| 5 | Si | 2,3-Naphthalene ring | $-Si(CH_3)_2(CH_2)_3NH.COO-$ | 1 | $-(C_2H_4O)_y-$ [MW ca. 2000] | $-CH_3$ | 2 | — | 0 | COONa | 4 |
| 6 | Si | 2,3-Naphthalene ring | $-Si(CH_3)_2(CH_2)_3NH.COO-$ | 1 | $-(C_2H_4O)_y-$ [MW ca. 750] | $-CH_3$ | 2 | — | 0 | COONa | 4 |
| 7 | Si | 2,3-Naphthalene ring | $-Si(CH_3)_2(CH_2)_3NH.COO-$ | 1 | $-(C_2H_4O)_y-$ [MW ca. 2000] | $-CH_3$ | 2 | —S—C6H5 | 1 | COONa | 8 |
| 8 | Si | 2,3-Naphthalene ring | $-Si(CH_3)_2(CH_2)_3NH.COO-$ | 1 | $-(C_2H_4O)_y-$ [MW ca. 350] | $-CH_3$ | 2 | —S—C6H5 | 1 | COONa | 8 |
| 9 | Si | 2,3-Naphthalene ring | $-Si(CH_3)_2.O-$ | 1 | $-(C_2H_4O)_y-$ [MW ca. 2000] | $-CH_3$ | 2 | — | 0 | COONa | 4 |
| 10 | Si | 2,3-Naphthalene ring | $-Si(CH_3)_2.O-$ | 1 | $-(C_2H_4O)_y-$ [MW ca. 750] | $-CH_3$ | 2 | — | 0 | COONa | 4 |
| 11 | Si | 2,3-Naphthalene ring | $-Si(CH_3)_2.O-$ | 1 | $-(C_2H_4O)_y-$ [MW ca. 750] | $-CH_3$ | 2 | —S—C6H5 | 1 | COONa | 8 |
| 12 | Si | 2,3-Naphthalene ring | $-Si(CH_3)_2.O-$ | 1 | $-(C_2H_4O)_y-$ [MW ca. 350] | $-CH_3$ | 2 | —S—C6H5 | 1 | COONa | 8 |
| 13 | Si | 2,3-Naphthalene ring | $-Si(CH_3)_2.NH-$ | 1 | $-(C_2H_4O)_y-$ [MW ca. 5000] | $-CH_3$ | 2 | — | 0 | COONa | 4 |

TABLE 1-continued

| No. | M | A | L | k | $-(C_xH_{2x}O)_y-$ | R$^1$ | p | XQ or Q | m | EZ | 4n |
|---|---|---|---|---|---|---|---|---|---|---|---|
| 14 | Si | 2,3-Naphthalene ring | $-Si(CH_3)_2-NH-$ | 1 | $-(C_2H_4O)_y-$ [MW ca. 750] | $-CH_3$ | 2 | — | 0 | COONa | 4 |
| 15 | Si | 2,3-Naphthalene ring | $-Si(CH_3)_2-NH-$ | 1 | $-(C_2H_4O)_y-$ [MW ca. 2000] | $-CH_3$ | 2 | phenyl-S- | 1 | COONa | 8 |
| 16 | Si | 2,3-Naphthalene ring | $-Si(CH_3)_2-NH-$ | 1 | $-(C_2H_4O)_y-$ [MW ca. 550] | $-CH_3$ | 2 | phenyl-S- | 1 | COONa | 8 |
| 17 | Si | 2,3-Naphthalene ring | — | 0 | $-(C_2H_4O)_y-$ [MW ca. 2000] | $-CH_3$ | 2 | — | 0 | COONa | 4 |
| 18 | Si | 2,3-Naphthalene ring | — | 0 | $-(C_2H_4O)_y-$ [MW ca. 550] | $-CH_3$ | 2 | — | 0 | COONa | 4 |
| 19 | Si | 2,3-Naphthalene ring | — | 0 | $-(C_2H_4O)_y-$ [MW ca. 2000] | $-CH_3$ | 2 | phenyl-S- | 1 | COONa | 8 |
| 20 | Si | 2,3-Naphthalene ring | — | 0 | $-(C_2H_4O)_y-$ [MW ca. 350] | $-CH_3$ | 2 | phenyl-S- | 1 | COONa | 8 |
| 21 | Si | 2,3-Naphthalene ring | — | 0 | $-(C_2H_4O)_y-$ [MW ca. 2000] | $-CH_2-$(tetrahydrofuran-2-yl) | 2 | — | 0 | COONa | 4 |
| 22 | Si | 2,3-Naphthalene ring | — | 0 | $-(C_3H_6O)_y-$ [MW ca. 2000] | $-CH_3$ | 2 | — | 0 | COONa | 4 |
| 23 | Ge | 2,3-Naphthalene ring | — | 0 | $-(C_2H_4O)_y-$ [MW ca. 2000] | $-CH_3$ | 2 | — | 0 | COONa | 4 |
| 24 | Al | 2,3-Naphthalene ring | — | 0 | $-(C_2H_4O)_y-$ [MW ca. 2000] | $-CH_3$ | 1 | — | 0 | COONa | 4 |
| 25 | Ga | 2,3-Naphthalene ring | — | 0 | $-(C_2H_4O)_y-$ [MW ca. 2000] | $-CH_3$ | 1 | — | 0 | COONa | 4 |
| 26 | Si | 2,3-Naphthalene ring | — | 0 | $-(C_2H_4O)_y-$ [MW ca. 2000] | $-CH_3$ | 2 | phenyl-S- | 1 | SO$_3$Na | 8 |

TABLE 1-continued

| No. | M | A | L | k | $-(C_xH_{2x}O)_y-$ | $R^1$ | p | XQ or Q | m | EZ | 4n |
|---|---|---|---|---|---|---|---|---|---|---|---|
| 27 | Si | 2,3-Naphthalene ring | — | 0 | $-(C_2H_4O)_y-$ [MW ca. 2000] | $-CH_3$ | 2 | $-S-\bigcirc$ | 1 | $OPO_3Na$ | 8 |
| 28 | Si | 2,3-Naphthalene ring | — | 0 | $-(C_2H_4O)_y-$ [MW ca. 2000] | $-CH_3$ | 2 | $\bigcirc$ | 1 | $SO_3-\begin{array}{c}COONa\\COONa\\COONa\end{array}$ | 6 |
| 29 | Si | 2,3-Naphthalene ring | — | 0 | $-(C_2H_4O)_y-$ [MW ca. 2000] | $-CH_3$ | 2 | $-SC_2H_4-$ | 1 | COONa | 4 |
| 30 | Si | 2,3-Naphthalene ring | — | 0 | $-(C_2H_4O)_y-$ [MW ca. 2000] | $-CH_3$ | 2 | $-O-\bigcirc$ | 1 | $CO_2(C_2H_4O)_dH$ [MW ca. 200] | 8 |
| 31 | Si | 2,3-Quinoline ring | $-Si(CH_3)_2-(CH_2)_3NH-$ | 1 | $-(C_2H_4O)_y-$ [MW ca. 2000] | $-CH_3$ | 2 | — | 0 | COONa | 4 |
| 32 | Si | 2,3-Quinoline ring | $-Si(CH_3)_2-(CH_2)_3NH-$ | 1 | $-(C_2H_4O)_y-$ [MW ca. 550] | $-CH_3$ | 2 | — | 0 | COONa | 4 |
| 33 | Si | 2,3-Quinoline ring | $-Si(CH_3)_2-(CH_2)_3NH-$ | 1 | $-(C_2H_4O)_y-$ [MW ca. 2000] | $-CH_3$ | 2 | $-S-\bigcirc$ | 1 | COONa | 8 |
| 34 | Si | 2,3-Quinoline ring | $-Si(CH_3)_2-(CH_2)_3NH-$ | 1 | $-(C_2H_4O)_y-$ [MW ca. 750] | $-CH_3$ | 2 | $-S-\bigcirc$ | 1 | COONa | 8 |
| 35 | Si | 2,3-Quinoline ring | $-Si(CH_3)_2-(CH_2)_3NH.COO-$ | 1 | $-(C_2H_4O)_y-$ [MW ca. 2000] | $-CH_3$ | 2 | — | 0 | COONa | 4 |
| 36 | Si | 2,3-Quinoline ring | $-Si(CH_3)_2-(CH_2)_3NH.COO-$ | 1 | $-(C_2H_4O)_y-$ [MW ca. 750] | $-CH_3$ | 2 | — | 0 | COONa | 4 |
| 37 | Si | 2,3-Quinoline ring | $-Si(CH_3)_2-(CH_2)_3NH.COO-$ | 1 | $-(C_2H_4O)_y-$ [MW ca. 2000] | $-CH_3$ | 2 | $-S-\bigcirc$ | 1 | COONa | 8 |
| 38 | Si | 2,3-Quinoline ring | $-Si(CH_3)_2-(CH_2)_3NH.COO-$ | 1 | $-(C_2H_4O)_y-$ [MW ca. 350] | $-CH_3$ | 2 | $-S-\bigcirc$ | 1 | COONa | 8 |

TABLE 1-continued

| No. | M | A | L | k | $-(C_xH_{2x}O)_y-$ | $R^1$ | p | XQ or Q | m | EZ | 4n |
|---|---|---|---|---|---|---|---|---|---|---|---|
| 39 | Si | 2,3-Quinoline ring | $-Si(CH_3)_2-O-$ | 1 | $-(C_2H_4O)_y-$ [MW ca. 2000] | $-CH_3$ | 2 | — | 0 | COONa | 4 |
| 40 | Si | 2,3-Quinoline ring | $-Si(CH_3)_2-O-$ | 1 | $-(C_2H_4O)_y-$ [MW ca. 750] | $-CH_3$ | 2 | — | 0 | COONa | 4 |
| 41 | Si | 2,3-Quinoline ring | $-Si(CH_3)_2-O-$ | 1 | $-(C_2H_4O)_y-$ [MW ca. 750] | $-CH_3$ | 2 | 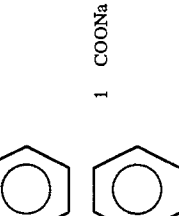$-S-$ | 1 | COONa | 8 |
| 42 | Si | 2,3-Quinoline ring | $-Si(CH_3)_2-O-$ | 1 | $-(C_2H_4O)_y-$ [MW ca. 350] | $-CH_3$ | 2 | 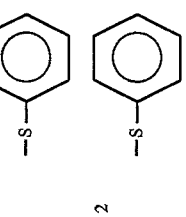$-S-$ | 1 | COONa | 8 |
| 43 | Si | 2,3-Quinoline ring | $-Si(CH_3)_2-NH-$ | 1 | $-(C_2H_4O)_y-$ [MW ca. 5000] | $-CH_3$ | 2 | — | 0 | COONa | 4 |
| 44 | Si | 2,3-Quinoline ring | $-Si(CH_3)_2-NH-$ | 1 | $-(C_2H_4O)_y-$ [MW ca. 750] | $-CH_3$ | 2 | — | 0 | COONa | 4 |
| 45 | Si | 2,3-Quinoline ring | $-Si(CH_3)_2-NH-$ | 1 | $-(C_2H_4O)_y-$ [MW ca. 2000] | $-CH_3$ | 2 | 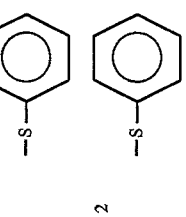$-S-$ | 1 | COONa | 8 |
| 46 | Si | 2,3-Quinoline ring | $-Si(CH_3)_2-NH-$ | 1 | $-(C_2H_4O)_y-$ [MW ca. 550] | $-CH_3$ | 2 | 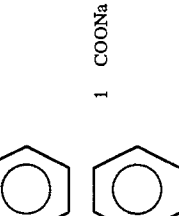$-S-$ | 1 | COONa | 8 |
| 47 | Si | 2,3-Quinoline ring | — | 0 | $-(C_2H_4O)_y-$ [MW ca. 2000] | $-CH_3$ | 2 | — | 0 | COONa | 4 |
| 48 | Si | 2,3-Quinoline ring | — | 0 | $-(C_2H_4O)_y-$ [MW ca. 550] | $-CH_3$ | 2 | — | 0 | COONa | 4 |
| 49 | Si | 2,3-Quinoline ring | — | 0 | $-(C_2H_4O)_y-$ [MW ca. 2000] | $-CH_3$ | 2 | 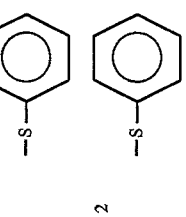$-S-$ | 1 | COONa | 8 |
| 50 | Si | 2,3-Quinoline ring | — | 0 | $-(C_2H_4O)_y-$ [MW ca. 350] | $-CH_3$ | 2 | 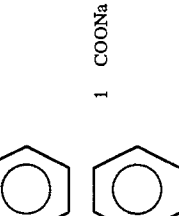$-S-$ | 1 | COONa | 8 |
| 51 | Si | 2,3-Quinoline ring | — | 0 | $-(C_2H_4O)_y-$ [MW ca. 2000] | 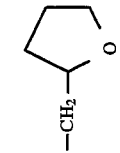 | 2 | — | 0 | COONa | 4 |

TABLE 1-continued

| No. | M | A | L | k | $-(C_xH_{2x}O)_y-$ | $R^1$ | p | XQ or Q | m | EZ | 4n |
|---|---|---|---|---|---|---|---|---|---|---|---|
| 52 | Si | 2,3-Quinoline ring | — | 0 | $-(C_2H_4O)_y-$ [MW ca. 2000] | $-CH_3$ | 2 | — | 0 | COONa | 4 |
| 53 | Ge | 2,3-Quinoline ring | — | 0 | $-(C_2H_4O)_y-$ [MW ca. 2000] | $-CH_3$ | 2 | — | 0 | COONa | 4 |
| 54 | Al | 2,3-Quinoline ring | — | 0 | $-(C_2H_4O)_y-$ [MW ca. 2000] | $-CH_3$ | 1 | — | 0 | COONa | 4 |
| 55 | Ga | 2,3-Quinoline ring | — | 0 | $-(C_2H_4O)_y-$ [MW ca. 2000] | $-CH_3$ | 1 | — | 0 | COONa | 4 |
| 56 | Si | 2,3-Quinoline ring | — | 0 | $-(C_2H_4O)_y-$ [MW ca. 2000] | $-CH_3$ | 2 |  | 1 | $SO_3Na$ | 8 |
| 57 | Si | 2,3-Quinoline ring | — | 0 | $-(C_2H_4O)_y-$ [MW ca. 2000] | $-CH_3$ | 2 |  | 1 | $OPO_3Na$ | 8 |
| 58 | Si | 2,3-Quinoline ring | — | 0 | $-(C_2H_4O)_y-$ [MW ca. 2000] | $-CH_3$ | 2 |  | 1 | $SO_3\overset{COONa}{\underset{COONa}{-}}COONa$ | 6 |
| 59 | Si | 2,3-Quinoline ring | — | 0 | $-(C_2H_4O)_y-$ [MW ca. 2000] | $-CH_3$ | 2 | $-SC_2H_4-$ | 1 | COONa | 4 |
| 60 | Si | 2,3-Quinoline ring | — | 0 | $-(C_2H_4O)_y-$ [MW ca. 2000] | $-CH_3$ | 2 |  | 1 | $CO_2(C_2H_4O)\mu H$ [MW ca. 200] | 8 |
| 61 | Si | 9,10-Phenanthrene ring | $-Si(CH_3)_2(CH_2)_3NH-$ | 1 | $-(C_2H_4O)_y-$ [MW ca. 2000] | $-CH_3$ | 2 | — | 0 | COONa | 4 |
| 62 | Si | 9,10-Phenanthrene ring | $-Si(CH_3)_2(CH_2)_3NH-$ | 1 | $-(C_2H_4O)_y-$ [MW ca. 550] | $-CH_3$ | 2 | — | 0 | COONa | 4 |
| 63 | Si | 9,10-Phenanthrene ring | $-Si(CH_3)_2(CH_2)_3NH-$ | 1 | $-(C_2H_4O)_y-$ [MW ca. 2000] | $-CH_3$ | 2 |  | 1 | COONa | 8 |
| 64 | Si | 9,10-Phenanthrene ring | $-Si(CH_3)_2(CH_2)_3NH-$ | 1 | $-(C_2H_4O)_y-$ [MW ca. 750] | $-CH_3$ | 2 |  | 2 | COONa | 16 |

| No. | M | A | L | k | —(C$_x$H$_{zx}$O)$_y$— | R¹ | p | XQ or Q | m | EZ | 4n |
|---|---|---|---|---|---|---|---|---|---|---|---|
| 65 | Si | 9,10-Phenanthrene ring | —Si(CH$_3$)$_2$·(CH$_2$)$_3$NH·COO— | 1 | —(C$_2$H$_4$O)$_y$— [MW ca. 2000] | —CH$_3$ | 2 | — | 0 | COONa | 4 |
| 66 | Si | 9,10-Phenanthrene ring | —Si(CH$_3$)$_2$·(CH$_2$)$_3$NH·COO— | 1 | —(C$_2$H$_4$O)$_y$— [MW ca. 750] | —CH$_3$ | 2 | — | 0 | COONa | 4 |
| 67 | Si | 9,10-Phenanthrene ring | —Si(CH$_3$)$_2$·(CH$_2$)$_3$NH·COO— | 1 | —(C$_2$H$_4$O)$_y$— [MW ca. 2000] | —CH$_3$ | 2 | —S—C$_6$H$_5$ | 2 | COONa | 8 |
| 68 | Si | 9,10-Phenanthrene ring | —Si(CH$_3$)$_2$·(CH$_2$)$_3$NH·COO— | 1 | —(C$_2$H$_4$O)$_y$— [MW ca. 350] | —CH$_3$ | 2 | —S—C$_6$H$_5$ | 2 | COONa | 16 |
| 69 | Si | 9,10-Phenanthrene ring | —Si(CH$_3$)$_2$·O— | 1 | —(C$_2$H$_4$O)$_y$— [MW ca. 2000] | —CH$_3$ | 2 | — | 0 | COONa | 4 |
| 70 | Si | 9,10-Phenanthrene ring | —Si(CH$_3$)$_2$·O— | 1 | —(C$_2$H$_4$O)$_y$— [MW ca. 750] | —CH$_3$ | 2 | — | 0 | COONa | 4 |
| 71 | Si | 9,10-Phenanthrene ring | —Si(CH$_3$)$_2$·O— | 1 | —(C$_2$H$_4$O)$_y$— [MW ca. 2000] | —CH$_3$ | 2 | —S—C$_6$H$_5$ | 1 | COONa | 8 |
| 72 | Si | 9,10-Phenanthrene ring | —Si(CH$_3$)$_2$·O— | 1 | —(C$_2$H$_4$O)$_y$— [MW ca. 350] | —CH$_3$ | 2 | —S—C$_6$H$_5$ | 2 | COONa | 16 |
| 73 | Si | 9,10-Phenanthrene ring | —Si(CH$_3$)$_2$·NH— | 1 | —(C$_2$H$_4$O)$_y$— [MW ca. 5000] | —CH$_3$ | 2 | — | 0 | COONa | 4 |
| 74 | Si | 9,10-Phenanthrene ring | —Si(CH$_3$)$_2$·NH— | 1 | —(C$_2$H$_4$O)$_y$— [MW ca. 750] | —CH$_3$ | 2 | — | 0 | COONa | 4 |
| 75 | Si | 9,10-Phenanthrene ring | —Si(CH$_3$)$_2$·NH— | 1 | —(C$_2$H$_4$O)$_y$— [MW ca. 2000] | —CH$_3$ | 2 | —S—C$_6$H$_5$ | 1 | COONa | 8 |
| 76 | Si | 9,10-Phenanthrene ring | —Si(CH$_3$)$_2$·NH— | 1 | —(C$_2$H$_4$O)$_y$— [MW ca. 550] | —CH$_3$ | 2 | —S—C$_6$H$_5$ | 2 | COONa | 16 |
| 77 | Si | 9,10-Phenanthrene ring | — | 0 | —(C$_2$H$_4$O)$_y$— [MW ca. 2000] | —CH$_3$ | 2 | — | 0 | COONa | 4 |
| 78 | Si | 9,10-Phenanthrene ring | — | 0 | —(C$_2$H$_4$O)$_y$— [MW ca. 550] | —CH$_3$ | 2 | — | 0 | COONa | 4 |

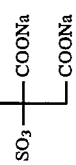

TABLE 1-continued

| No. | M | A | L | k | $-(C_xH_{2x}O_y)-$ | $R^1$ | p | XQ or Q | m | EZ | 4n |
|---|---|---|---|---|---|---|---|---|---|---|---|
| 91 | Si | 2,3-Anthracene ring | $-Si(CH_3)_2.(CH_2)_3NH-$ | 1 | $-(C_2H_4O)_y-$ [MW ca. 2000] | $-CH_3$ | 2 | — | 0 | COONa | 4 |
| 92 | Si | 2,3-Anthracene ring | $-Si(CH_3)_2.(CH_2)_3NH-$ | 1 | $-(C_2H_4O)_y-$ [MW ca. 550] | $-CH_3$ | 2 | — | 0 | COONa | 4 |
| 93 | Si | 2,3-Anthracene ring | $-Si(CH_3)_2.(CH_2)_3NH-$ | 1 | $-(C_2H_4O)_y-$ [MW ca. 2000] | $-CH_3$ | 2 | —S—⟨Ph⟩ | 1 | COONa | 8 |
| 94 | Si | 2,3-Anthracene ring | $-Si(CH_3)_2.(CH_2)_3NH-$ | 1 | $-(C_2H_4O)_y-$ [MW ca. 750] | $-CH_3$ | 2 | —S—⟨Ph⟩ | 2 | COONa | 16 |
| 95 | Si | 2,3-Anthracene ring | $-Si(CH_3)_2.(CH_2)_3NH.COO-$ | 1 | $-(C_2H_4O)_y-$ [MW ca. 2000] | $-CH_3$ | 2 | — | 0 | COONa | 4 |
| 96 | Si | 2,3-Anthracene ring | $-Si(CH_3)_2.(CH_2)_3NH.COO-$ | 1 | $-(C_2H_4O)_y-$ [MW ca. 750] | $-CH_3$ | 2 | — | 0 | COONa | 4 |
| 97 | Si | 2,3-Anthracene ring | $-Si(CH_3)_2.(CH_2)_3NH.COO-$ | 1 | $-(C_2H_4O)_y-$ [MW ca. 350] | $-CH_3$ | 2 | —S—⟨Ph⟩ | 2 | COONa | 8 |
| 98 | Si | 2,3-Anthracene ring | $-Si(CH_3)_2.(CH_2)_3NH.COO-$ | 1 | $-(C_2H_4O)_y-$ [MW ca. 2000] | $-CH_3$ | 2 | —S—⟨Ph⟩ | 2 | COONa | 16 |
| 99 | Si | 2,3-Anthracene ring | $-Si(CH_3)_2.O-$ | 1 | $-(C_2H_4O)_y-$ [MW ca. 2000] | $-CH_3$ | 2 | — | 0 | COONa | 4 |
| 100 | Si | 2,3-Anthracene ring | $-Si(CH_3)_2.O-$ | 1 | $-(C_2H_4O)_y-$ [MW ca. 750] | $-CH_3$ | 2 | — | 0 | COONa | 4 |
| 101 | Si | 2,3-Anthracene ring | $-Si(CH_3)_2.O-$ | 1 | $-(C_2H_4O)_y-$ [MW ca. 350] | $-CH_3$ | 2 | —S—⟨Ph⟩ | 1 | COONa | 8 |
| 102 | Si | 2,3-Anthracene ring | $-Si(CH_3)_2.O-$ | 1 | $-(C_2H_4O)_y-$ [MW ca. 750] | $-CH_3$ | 2 | —S—⟨Ph⟩ | 2 | COONa | 16 |
| 103 | Si | 2,3-Anthracene ring | $-Si(CH_3)_2.NH-$ | 1 | $-(C_2H_4O)_y-$ [MW ca. 5000] | $-CH_3$ | 2 | — | 0 | COONa | 4 |
| 104 | Si | 2,3-Anthracene ring | $-Si(CH_3)_2.NH-$ | 1 | $-(C_2H_4O)_y-$ [MW ca. 750] | $-CH_3$ | 2 | — | 0 | COONa | 4 |

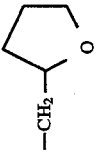

TABLE 1-continued

| No. | M | A | L | k | $-(C_xH_xO)_y-$ | $R^1$ | p | XQ or Q | m | EZ | 4n |
|---|---|---|---|---|---|---|---|---|---|---|---|
| 118 | Si | 2,3-Anthracene ring | — | 0 | $-(C_2H_4O)_y-$ [MW ca. 2000] | $-CH_3$ | 2 | 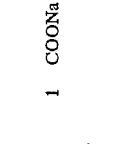 | 1 | $SO_3$ —COONa / —COONa / —COONa | 6 |
| 119 | Si | 2,3-Anthracene ring | — | 0 | $-(C_2H_4O)_y-$ [MW ca. 2000] | $-CH_3$ | 2 | $-SC_2H_4-$ | 2 | COONa | 8 |
| 120 | Si | 2,3-Anthracene ring | — | 0 | $-(C_2H_4O)_y-$ [MW ca. 2000] | $-CH_3$ | 2 | 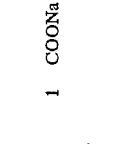 —O— | 1 | $CO_2(C_2H_4O)_4H$ [MW ca. 200] | 8 |
| 121 | Si | 1,2-Naphthalene ring | $-Si(CH_3)_2(CH_2)_3NH-$ | 1 | $-(C_2H_4O)_y-$ [MW ca. 2000] | $-CH_3$ | 2 | — | 0 | COONa | 4 |
| 122 | Si | 1,2-Naphthalene ring | $-Si(CH_3)_2(CH_2)_3NH-$ | 1 | $-(C_2H_4O)_y-$ [MW ca. 550] | $-CH_3$ | 2 | — | 0 | COONa | 4 |
| 123 | Si | 1,2-Naphthalene ring | $-Si(CH_3)_2(CH_2)_3NH-$ | 1 | $-(C_2H_4O)_y-$ [MW ca. 2000] | $-CH_3$ | 2 | 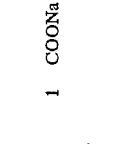 —S— | 1 | COONa | 8 |
| 124 | Si | 1,2-Naphthalene ring | $-Si(CH_3)_2(CH_2)_3NH-$ | 1 | $-(C_2H_4O)_y-$ [MW ca. 750] | $-CH_3$ | 2 | 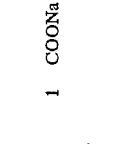 —S— | 1 | COONa | 8 |
| 125 | Si | 1,2-Naphthalene ring | $-Si(CH_3)_2(CH_2)_3NH.COO-$ | 1 | $-(C_2H_4O)_y-$ [MW ca. 2000] | $-CH_3$ | 2 | — | 0 | COONa | 4 |
| 126 | Si | 1,2-Naphthalene ring | $-Si(CH_3)_2(CH_2)_3NH.COO-$ | 1 | $-(C_2H_4O)_y-$ [MW ca. 750] | $-CH_3$ | 2 | — | 0 | COONa | 4 |
| 127 | Si | 1,2-Naphthalene ring | $-Si(CH_3)_2(CH_2)_3NH.COO-$ | 1 | $-(C_2H_4O)_y-$ [MW ca. 2000] | $-CH_3$ | 2 | 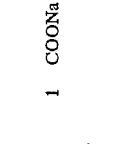 —S— | 1 | COONa | 8 |
| 128 | Si | 1,2-Naphthalene ring | $-Si(CH_3)_2(CH_2)_3NH.COO-$ | 1 | $-(C_2H_4O)_y-$ [MW ca. 350] | $-CH_3$ | 2 | 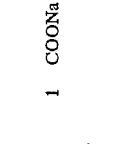 —S— | 1 | COONa | 8 |
| 129 | Si | 1,2-Naphthalene ring | $-Si(CH_3)_2-O-$ | 1 | $-(C_2H_4O)_y-$ [MW ca. 2000] | $-CH_3$ | 2 | — | 0 | COONa | 4 |
| 130 | Si | 1,2-Naphthalene ring | $-Si(CH_3)_2-O-$ | 1 | $-(C_2H_4O)_y-$ [MW ca. 750] | $-CH_3$ | 2 | — | 0 | COONa | 4 |

TABLE 1-continued

| No. | M | A | L | k | $-(C_xH_{2x}O)_y-$ | $R^1$ | p | XQ or Q | m | EZ | 4n |
|---|---|---|---|---|---|---|---|---|---|---|---|
| 131 | Si | 1,2-Naphthalene ring | $-Si(CH_3)_2O-$ | 1 | $-(C_2H_4O)_y-$ [MW ca. 750] | $-CH_3$ | 2 | phenyl-S— | 1 | COONa | 8 |
| 132 | Si | 1,2-Naphthalene ring | $-Si(CH_3)_2O-$ | 1 | $-(C_2H_4O)_y-$ [MW ca. 350] | $-CH_3$ | 2 | phenyl-S— | 1 | COONa | 8 |
| 133 | Si | 1,2-Naphthalene ring | $-Si(CH_3)_2NH-$ | 1 | $-(C_2H_4O)_y-$ [MW ca. 5000] | $-CH_3$ | 2 | — | 0 | COONa | 4 |
| 134 | Si | 1,2-Naphthalene ring | $-Si(CH_3)_2NH-$ | 1 | $-(C_2H_4O)_y-$ [MW ca. 750] | $-CH_3$ | 2 | — | 0 | COONa | 4 |
| 135 | Si | 1,2-Naphthalene ring | $-Si(CH_3)_2NH-$ | 1 | $-(C_2H_4O)_y-$ [MW ca. 2000] | $-CH_3$ | 2 | phenyl-S— | 1 | COONa | 8 |
| 136 | Si | 1,2-Naphthalene ring | $-Si(CH_3)_2NH-$ | 1 | $-(C_2H_4O)_y-$ [MW ca. 550] | $-CH_3$ | 2 | phenyl-S— | 1 | COONa | 8 |
| 137 | Si | 1,2-Naphthalene ring | — | 0 | $-(C_2H_4O)_y-$ [MW ca. 2000] | $-CH_3$ | 2 | — | 0 | COONa | 4 |
| 138 | Si | 1,2-Naphthalene ring | — | 0 | $-(C_2H_4O)_y-$ [MW ca. 550] | $-CH_3$ | 2 | — | 0 | COONa | 4 |
| 139 | Si | 1,2-Naphthalene ring | — | 0 | $-(C_2H_4O)_y-$ [MW ca. 2000] | $-CH_3$ | 2 | phenyl-S— | 1 | COONa | 8 |
| 140 | Si | 1,2-Naphthalene ring | — | 0 | $-(C_2H_4O)_y-$ [MW ca. 350] | $-CH_3$ | 2 | phenyl-S— | 1 | COONa | 8 |
| 141 | Si | 1,2-Naphthalene ring | — | 0 | $-(C_2H_4O)_y-$ [MW ca. 2000] | tetrahydrofuranyl-CH$_2$— | 2 | — | 0 | COONa | 4 |
| 142 | Si | 1,2-Naphthalene ring | — | 0 | $-(C_3H_6O)_y-$ [MW ca. 2000] | $-CH_3$ | 2 | — | 0 | COONa | 4 |
| 143 | Ge | 1,2-Naphthalene ring | — | 0 | $-(C_2H_4O)_y-$ [MW ca. 2000] | $-CH_3$ | 2 | — | 0 | COONa | 4 |

TABLE 1-continued

| No. | M | A | L | k | $-(C_xH_{2x}O)_y-$ | $R^1$ | p | XQ or Q | m | EZ | 4n |
|---|---|---|---|---|---|---|---|---|---|---|---|
| 144 | Al | 1,2-Naphthalene ring | — | 0 | $-(C_2H_4O)_y-$ [MW ca. 2000] | $-CH_3$ | 1 | — | 0 | COONa | 4 |
| 145 | Ga | 1,2-Naphthalene ring | — | 0 | $-(C_2H_4O)_y-$ [MW ca. 2000] | $-CH_3$ | 1 | — | 0 | COONa | 4 |
| 146 | Si | 1,2-Naphthalene ring | — | 0 | $-(C_2H_4O)_y-$ [MW ca. 2000] | $-CH_3$ | 2 | $-S-\mathrm{C_6H_5}$ | 1 | $SO_3Na$ | 8 |
| 147 | Si | 1,2-Naphthalene ring | — | 0 | $-(C_2H_4O)_y-$ [MW ca. 2000] | $-CH_3$ | 2 | $-S-\mathrm{C_6H_5}$ | 1 | $OPO_3Na$ | 8 |
| 148 | Si | 1,2-Naphthalene ring | — | 0 | $-(C_2H_4O)_y-$ [MW ca. 2000] | $-CH_3$ | 2 | $-S-\mathrm{C_6H_5}$ | 1 | $SO_3$—(COONa)(COONa)(COONa) | 6 |
| 149 | Si | 1,2-Naphthalene ring | — | 0 | $-(C_2H_4O)_y-$ [MW ca. 2000] | $-CH_3$ | 2 | $-SC_2H_4-$ | 1 | COONa | 4 |
| 150 | Si | 1,2-Naphthalene ring | — | 0 | $-(C_2H_4O)_y-$ [MW ca. 2000] | $-CH_3$ | 2 | $-O-\mathrm{C_6H_5}$ | 1 | $CO_2(C_2H_4O)_zH$ [MW ca. 200] | 8 |
| 151 | Si | 2,3-Quinoxaline ring | $-Si(CH_3)_2(CH_2)_3NH-$ | 1 | $-(C_2H_4O)_y-$ [MW ca. 2000] | $-CH_3$ | 2 | — | 0 | COONa | 4 |
| 152 | Si | 2,3-Quinoxaline ring | $-Si(CH_3)_2(CH_2)_3NH-$ | 1 | $-(C_2H_4O)_y-$ [MW ca. 550] | $-CH_3$ | 2 | — | 0 | COONa | 4 |
| 153 | Si | 2,3-Quinoxaline ring | $-Si(CH_3)_2(CH_2)_3NH-$ | 1 | $-(C_2H_4O)_y-$ [MW ca. 2000] | $-CH_3$ | 2 | $-S-\mathrm{C_6H_5}$ | 1 | COONa | 8 |
| 154 | Si | 2,3-Quinoxaline ring | $-Si(CH_3)_2(CH_2)_3NH-$ | 1 | $-(C_2H_4O)_y-$ [MW ca. 750] | $-CH_3$ | 2 | $-S-\mathrm{C_6H_5}$ | 1 | COONa | 8 |
| 155 | Si | 2,3-Quinoxaline ring | $-Si(CH_3)_2(CH_2)_3NH.COO-$ | 1 | $-(C_2H_4O)_y-$ [MW ca. 2000] | $-CH_3$ | 2 | — | 0 | COONa | 4 |
| 156 | Si | 2,3-Quinoxaline ring | $-Si(CH_3)_2(CH_2)_3NH.COO-$ | 1 | $-(C_2H_4O)_y-$ [MW ca. 750] | $-CH_3$ | 2 | — | 0 | COONa | 4 |

TABLE 1-continued

| No. | M | A | L | k | $-(C_xH_{2x}O)_y-$ | $R^1$ | p | XQ or Q | m | EZ | 4n |
|---|---|---|---|---|---|---|---|---|---|---|
| 157 | Si | 2,3-Quinoxaline ring | $-Si(CH_3)_2(CH_2)_3NH.COO-$ | 1 | $-(C_2H_4O)_y-$ [MW ca. 2000] | $-CH_3$ | 2 | 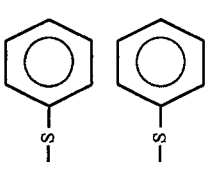 | 1 | COONa | 8 |
| 158 | Si | 2,3-Quinoxaline ring | $-Si(CH_3)_2(CH_2)_3NH.COO-$ | 1 | $-(C_2H_4O)_y-$ [MW ca. 350] | $-CH_3$ | 2 | 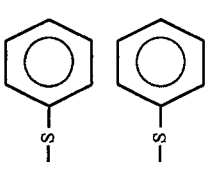 | 1 | COONa | 8 |
| 159 | Si | 2,3-Quinoxaline ring | $-Si(CH_3)_2.O-$ | 1 | $-(C_2H_4O)_y-$ [MW ca. 2000] | $-CH_3$ | 2 | — | 0 | COONa | 4 |
| 160 | Si | 2,3-Quinoxaline ring | $-Si(CH_3)_2.O-$ | 1 | $-(C_2H_4O)_y-$ [MW ca. 750] | $-CH_3$ | 2 | — | 0 | COONa | 4 |
| 161 | Si | 2,3-Quinoxaline ring | $-Si(CH_3)_2.O-$ | 1 | $-(C_2H_4O)_y-$ [MW ca. 750] | $-CH_3$ | 2 | 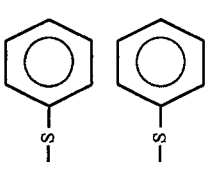 | 1 | COONa | 8 |
| 162 | Si | 2,3-Quinoxaline ring | $-Si(CH_3)_2.O-$ | 1 | $-(C_2H_4O)_y-$ [MW ca. 350] | $-CH_3$ | 2 | 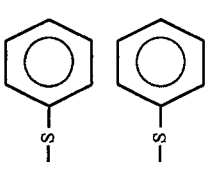 | 1 | COONa | 8 |
| 163 | Si | 2,3-Quinoxaline ring | $-Si(CH_3)_2.NH-$ | 1 | $-(C_2H_4O)_y-$ [MW ca. 5000] | $-CH_3$ | 2 | — | 0 | COONa | 4 |
| 164 | Si | 2,3-Quinoxaline ring | $-Si(CH_3)_2.NH-$ | 1 | $-(C_2H_4O)_y-$ [MW ca. 750] | $-CH_3$ | 2 | — | 0 | COONa | 4 |
| 165 | Si | 2,3-Quinoxaline ring | $-Si(CH_3)_2.NH-$ | 1 | $-(C_2H_4O)_y-$ [MW ca. 550] | $-CH_3$ | 2 | 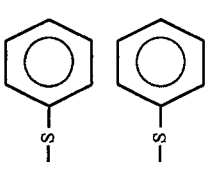 | 1 | COONa | 8 |
| 166 | Si | 2,3-Quinoxaline ring | $-Si(CH_3)_2.NH-$ | 1 | $-(C_2H_4O)_y-$ [MW ca. 2000] | $-CH_3$ | 2 | 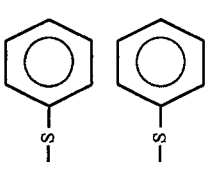 | 1 | COONa | 8 |
| 167 | Si | 2,3-Quinoxaline ring | — | 0 | $-(C_2H_4O)_y-$ [MW ca. 2000] | $-CH_3$ | 2 | — | 0 | COONa | 4 |
| 168 | Si | 2,3-Quinoxaline ring | — | 0 | $-(C_2H_4O)_y-$ [MW ca. 550] | $-CH_3$ | 2 | — | 0 | COONa | 4 |
| 169 | Si | 2,3-Quinoxaline ring | — | 0 | $-(C_2H_4O)_y-$ [MW ca. 2000] | $-CH_3$ | 2 | 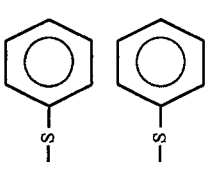 | 1 | COONa | 8 |

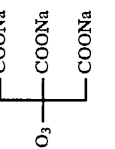

The water-soluble tetraazaporphin of the general formula (I) can be obtained by various synthetic methods. For example, it can be synthesized by the following routes:

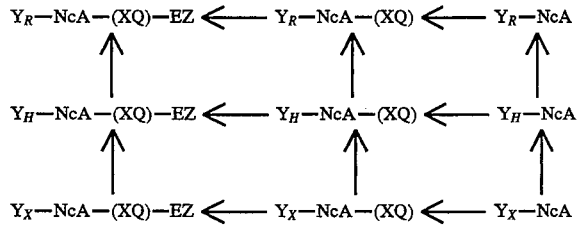

In the above formulae, NcA means the portion except for {$OL_K$—$C_xH_{2x}O)_y$—$R^1$}$_p$, —$(EZ)_n$ and XQ (including Q; hereinafter the same applied); $Y_R$—NcA—(XQ)—EZ is a compound of the general formula (I) wherein $Y_R$ is {$OL_K$—$C_xH_{2x}O)_y$—$R^1$}$_p$, bonded to M; $Y_H$—NcA—(XQ)—EZ is a compound of the general formula (I) wherein the substituent on M is not $Y_R$ but —OH; $Y_X$—NcA—(XQ)—EZ is a compound of the general formula (I) wherein the substituent on M is not $Y_R$ but a halogen atom; $Y_R$—NcA—(XQ) is a compound of the general formula (I) wherein {$OL_K$—$C_xH_{2x}O)_y$—$R^1$}$_p$ and XQ are present, said compound being able to have a substituent which can be introduced into EZ by hydrolysis on a fused polycyclic aromatic ring of NcA or XQ; $Y_H$—NcA—(XQ) is a compound of the general formula (I) wherein the substituent on M is —OH and XQ is present, said compound being able to have a substituent which can be introduced into EZ by hydrolysis on a fused polycyclic aromatic ring of NcA or XQ; $Y_X$—NcA—(XQ) is a compound of the general formula (I) wherein the substituent on M is a halogen atom and XQ is present, said compound being able to have a substituent which can be introduced into EZ by hydrolysis on a fused polycyclic aromatic ring of NcA or XQ; $Y_R$—NcA is a compound of the general formula (I) wherein {$OL_K$—$C_xH_{2x}O)_y$—$R^1$}$_p$ is present, said compound being able to have a leaving group which can be substituted with XQ; $Y_H$—NcA is a compound of the general formula (I) wherein the substituent on M is —OH, said compound being able to have a leaving group which can be substituted with xQ; and $Y_X$—NcA is a compound of the general formula (I) wherein the substituent on M is a halogen atom, said compound being able to have a leaving group which can be substituted with XQ.

The reactions of individual compounds in the above-mentioned routes are well known, but dependent on structures to be introduced. Further, preferable routes are dependent on the desired final products.

The reaction from the lowest compounds to upper compounds in the above-mentioned reaction routes, that is, the substitution from $Y_X$ to $Y_H$, can be carried out by hydrolysis. Further, the substitution from $Y_H$ to $Y_R$, can be carried out by reacting with a corresponding polyethylene glycol derivative, silanol, chlorosilane, or the like.

Further, in the above-mentioned reaction routes, the change of compounds from a right-hand side to a left-hand side, that is, the introduction of XQ and EZ, can be carried out by reacting with a compound having the desired XQ and/or EZ or having a moiety which can be changed to XQ or EZ by one step or a plurality of steps.

The compounds represented by $Y_X$—NcA—(XQ)—EZ, $Y_X$—NcA—(XQ) and $Y_X$—NcA mentioned above can be synthesized from a corresponding dicyano aromatic compounds or isoindoline derivatives according to the methods described in references [Zh. Obshch. Khim., 39, 2554–2558 (1969), J. Am. Chem. Soc. 106, 7404–7410 (1984), Zh. Obshch. Khim., 39, 2536–2541 (1969), Chem. Ber., 121, 1479–1486 (1988), Synthetic Metals, 9, 329–340 (1984), etc.].

A most important characteristic required of a compound used as the fluorochrome for labeling is that the compound shows a high fluorescence quantum yield (>0.1). For showing such a high fluorescence quantum yield, a tetraazaporphin derivative should satisfy the following conditions: the central metal should not be a heavy metal or a transition metal, and the tetraazaporphin derivative should be in a monomolecular state in a solution.

For satisfying these conditions, Al, Si, P, Ga, Ge or Sc is used as the central metal M. In particular, it is most preferable to make it possible to maintain the molecular state in a solution by suppressing the formation of face-to-face E-aggregates between molecules which is characteristic of tetraazaporphin, by using a compound containing a tetravalent metal (Si or Ge) as the central metal and having two substituents —$OL_K$—$(C_xH_{2x}O)_y$—$R^1$ on M above and below a tetraazaporphin ring. For realizing the monomolecular state in an aqueous solution, it is preferable to place a surfactant together with the fluorochrome for labeling. The concentration of the surfactant is preferably 0.01 to 5% by weight, more preferably 0.04 to 2% by weight.

The surfactant includes ionic surfactants and nonionic surfactants. Of these, nonionic surfactants such as Triton X-100, Tween series surfactants, Brij series surfactants, etc. are particularly preferable.

A tetraazaporphin which assumes a monomolecular state in the aqueous solution thus obtained is highly soluble particularly in water and polar organic solvents, is easy to separate and purify in its synthesis, and shows a high fluorescence quantum yield (>0.3) sufficient to permit application of the tetraazaporphin to fluorochrome for labeling. For these reasons, it is particularly preferable to use the water-soluble tetraazaporphin of this invention.

The above-mentioned fluorochrome for labeling can be made into a reagent for various fluorescence analyses. As described above, the reagent preferably contains a nonionic surfactant, depending on the kind of the fluorochrome.

In practice, said fluorochrome for labeling is made into a reagent by attaching the same to any of various substances, depending on the purpose of analysis. When the fluorochrome is used for immunoassay, the substances are various antigens (including haptens and drugs) and antibodies. When the fluorochrome is used for analyzing the nucleotide sequence of DNA or when it is used for analysis in the form of a DNA probe, the substance is the DNA, i.e., nucleotide.

The fluorochrome is often used particularly as a fluorescent label for substances derived from organisms, for example, in the above analyses.

The substance derived from an organism which can be labeled with the aforesaid fluorochrome for labeling and is used in this invention, includes proteins (peptides), nucleotides, sugars, lipids, hormones, vitamins, alkaloids, antibiotics, complexes thereof, etc. which are obtained from organisms such as animals, plants, microorganisms (including viruses), etc. These substances may be any of those extracted from natural sources, artificial and completely synthetic ones, and artificial and semisynthetic ones.

Specific examples of the proteins (peptides) are serum albumin, immunoglobulins (e.g. IgG, IgA, IgM, IgD and IgE), monoclonal antibodies against various proteins or membrane antigens of leucocyte, and enzymes (e.g. peroxidases, glucose oxidase and alkaline oxidases). Specific examples of the nucleotides are DNA, RNA, synthetic oligonucleotides, synthetic polynucleotides, ATP, CTP, GTP, TTP, UTP, dATP, dCTP, dGTP, dTTP, dUTP, ddATP, ddCTP, ddGTP, ddTTP, ddUTP, and derivatives thereof. Specific examples of the sugars are polysaccharides (e.g. glycogen, starch, and mannan), oligosaccharides, and monosaccharides (e.g. glucose and mannose). The lipids include phosphatidylcholine, phosphatidylethanolamine, fats, fatty acids, etc. The hormones include peptide hormones (e.g. insulin, growth hormone, oxytocin, vasopressin, secretin, epidermal growth factor, gastrin, glucagon and calcitonin), steroid hormones (e.g. androgen, estrogen and hydrocortisone), catecholamines (e.g. adrenaline and noradrenaline), etc. The vitamins include various vitamins such as vitamin A, vitamin B1, B2, B6 and B12, biotin, folic acid, vitamin C, vitamin D, vitamin E, etc. The alkaloids include opium alkaloids (e.g. morphine), tropane alkaloids (e.g. atropine and scopolamine), indole alkaloids (e.g. vinblastine and vincristine), isoquinoline alkaloids (e.g. coptis root), etc. The antibiotics include penicillin, cephalosporin, kanamycin, erythromycin, chloramphenicol, etc.

The substance derived from an organism and the fluorochrome for labeling can be combined by linking a functional group (e.g. a phosphoric acid group, carboxylic acid group, amino group, hydroxyl group or thiol group) in the substance derived from an organism and a functional group (e.g. a carboxyl group or a sulfonic acid group) in the fluorochrome for labeling, directly to each other through an ionic bond or a covalent bond. Alternatively, the substance derived from an organism and the fluorochrome for labeling can be combined through a combination assistant group called a linker, for facilitating bond-forming reaction. The substance derived from an organism which has been labeled with the fluorochrome for labeling can be purified by conventional purifying means such as chromatography, recrystallization, etc.

The aforesaid linker should be a group having at least two functional groups because one or more bonds should be formed for each of the substance derived from an organism and the fluorochrome for labeling. For this purpose, there can be used diols, diamines, amino alcohols, dicarboxylic acids, dithiols, aminocarboxylic acids, hydroxycarboxylic acids, etc.

The fluorochrome for labeling and the reagent comprising the same of this invention can be used in various fluorescence analysis method.

In particular, the compound of the general formula (I) absorbs semiconductor laser beams (670 to 840 nm) efficiently to emit fluorescence, and hence are very useful for assay of various antigens, drugs, DNAs, etc. and analysis of the nucleotide sequence of DNA (DNA sequencer) in which measurement is carried out using an inexpensive and compact semiconductor laser.

This invention is explained below with reference to Examples, which are not by way of limitation but by way of illustration.

SYNTHETIC EXAMPLE 1

Synthesis of 3,4-bis(dibromomethyl)bromobenzene

To a solution of 37 g (0.2 mol) of 4-bromo-o-xylene (75%) (mfd. by Aldrich Chemical Co.) and 142.4 g (0.8 mol) of N-bromosuccinimide in 500 ml of carbon tetrachloride was added 1 g of benzoyl peroxide, and the rusulting mixture was irradiated by a 100-W high pressure mercury arc lamp for 8 to 12 hours under reflux in an inner irradiating tube (mfd. by Ushio Inc.). After the mixture was allowed to cool, the white crystals precipitated were removed by filtration and the carbon tetrachloride solution, i.e., the mother liquor was concentrated under reduced pressure. The solid thus obtained was recrystallized from hexane/methylene chloride to obtain 64 g of 3,4-bis(dibromomethyl)bromobenzene as colorless crystals. Physical properties of 3,4-bis(dibromomethyl)bromobenzene were as follows:

(1) Melting point: 108.5°–110.5° C.
(2) Elementary analysis values:

TABLE 2

|  | C | H | Br |
| --- | --- | --- | --- |
| Calculated (%) | 19.19 | 1.01 | 79.80 |
| Found (%) | 19.12 | 0.88 | 79.84 |

(3) NMR spectrum values: $CDCl_3$ $\delta$ values: 7.81 (1H, br-s), 7.57 (1H, d, J=8.54 Hz), 7.50 (1H, dd, J=8.54, 1.83 Hz), 7.06 (1H, s), 7.02 (1H, s)

(4) IR spectrum (KBr) is shown in FIG. 1.

SYNTHETIC EXAMPLE 2

Synthesis of 6-bromo-2,3-dicyanonaphthalene

To a solution of 100.2 g (0.2 mol) of 3,4-bis(dibromomethyl)bromobenzene and 27 g (0.346 mol) of fumaronitrile in 800 ml of anhydrous N,N-dimethylformamide was added 200 g (0.67 mol) of sodium iodide with sufficient stirring, and the resulting mixture was stirred under nitrogen at about 75° C. for about 7 hours. After completion of the reaction, the reaction mixture was poured onto about 4 kg of ice. Sodium hydrogen-sulfite was slowly added until the reddish-brown aqueous solution thus obtained turned light-yellow. Sodium hydrogensulfite was added in a slight excess and stirred for a while. The resulting mixture was allowed to stand overnight at room temperature. The light-yellow solid precipitated was filtered by suction and sufficiently washed with water and then methanol. The light-yellow solid was recrystallized from acetone/ethanol to obtain 33 g of colorless needles. The crystals were confirmed to be 6-bromo-2,3-dicyanonaphthalene from the following analyses:

(1) Melting point: 254.5°–255.5° C.
(2) Elementary analysis values:

TABLE 3

|  | C | H | N | Br |
| --- | --- | --- | --- | --- |
| Calculated (%) | 56.06 | 1.96 | 10.90 | 31.08 |
| Found (%) | 55.99 | 1.67 | 10.87 | 30.74 |

Figure 2:
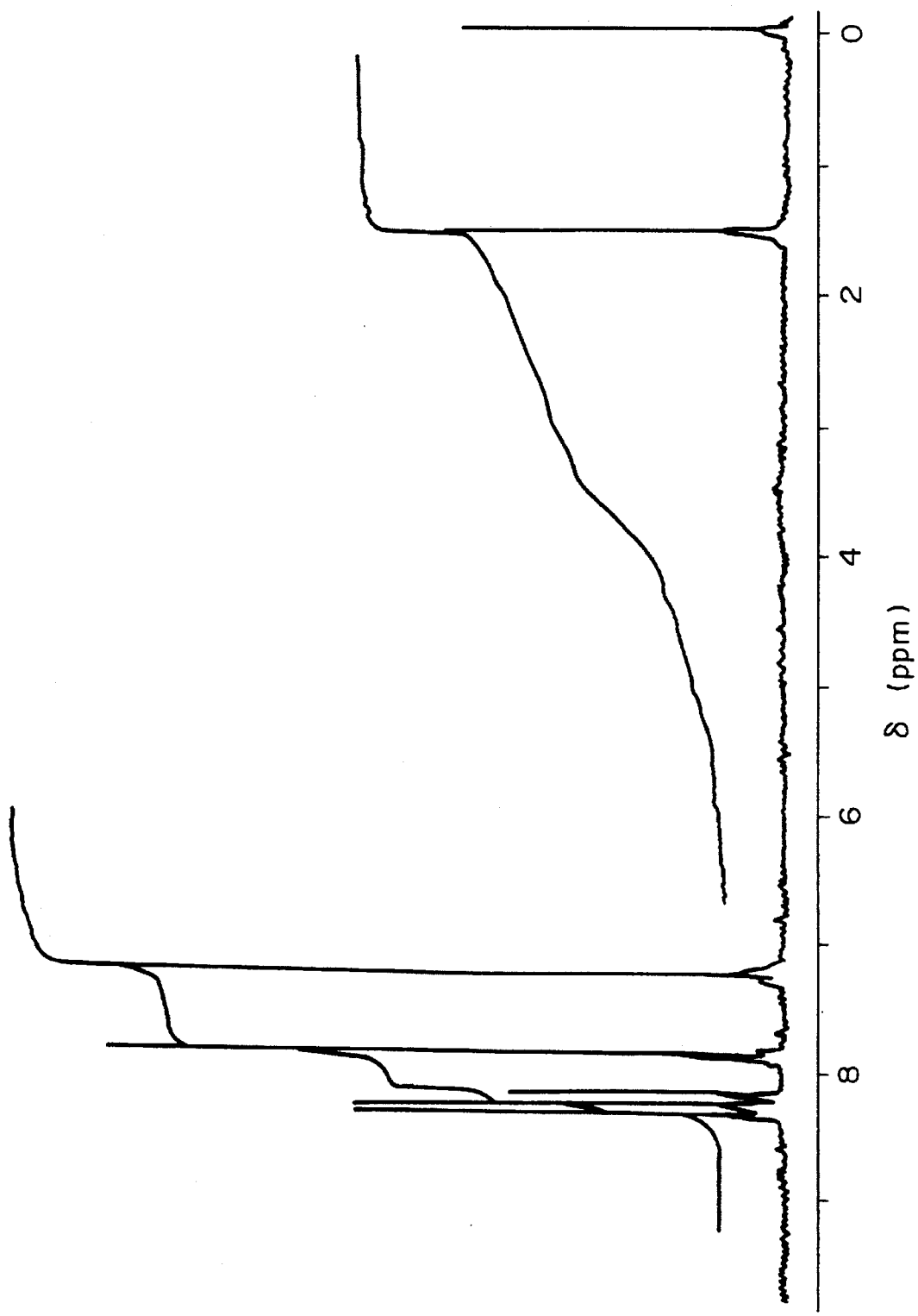
FIG. 2 is an NMR spectrum in $CDCl_3$ of 6-bromo-2,3-dicyanonaphthalene.

(3) NMR spectrum values: $CDCl_3$ (the NMR spectrum is shown in FIG. 2)

$\delta$ values: 8.34 (1H, s), 8.27 (1H, s), 8.17 (1H, br-s), 7.88 (2H, m)

Figure 3:
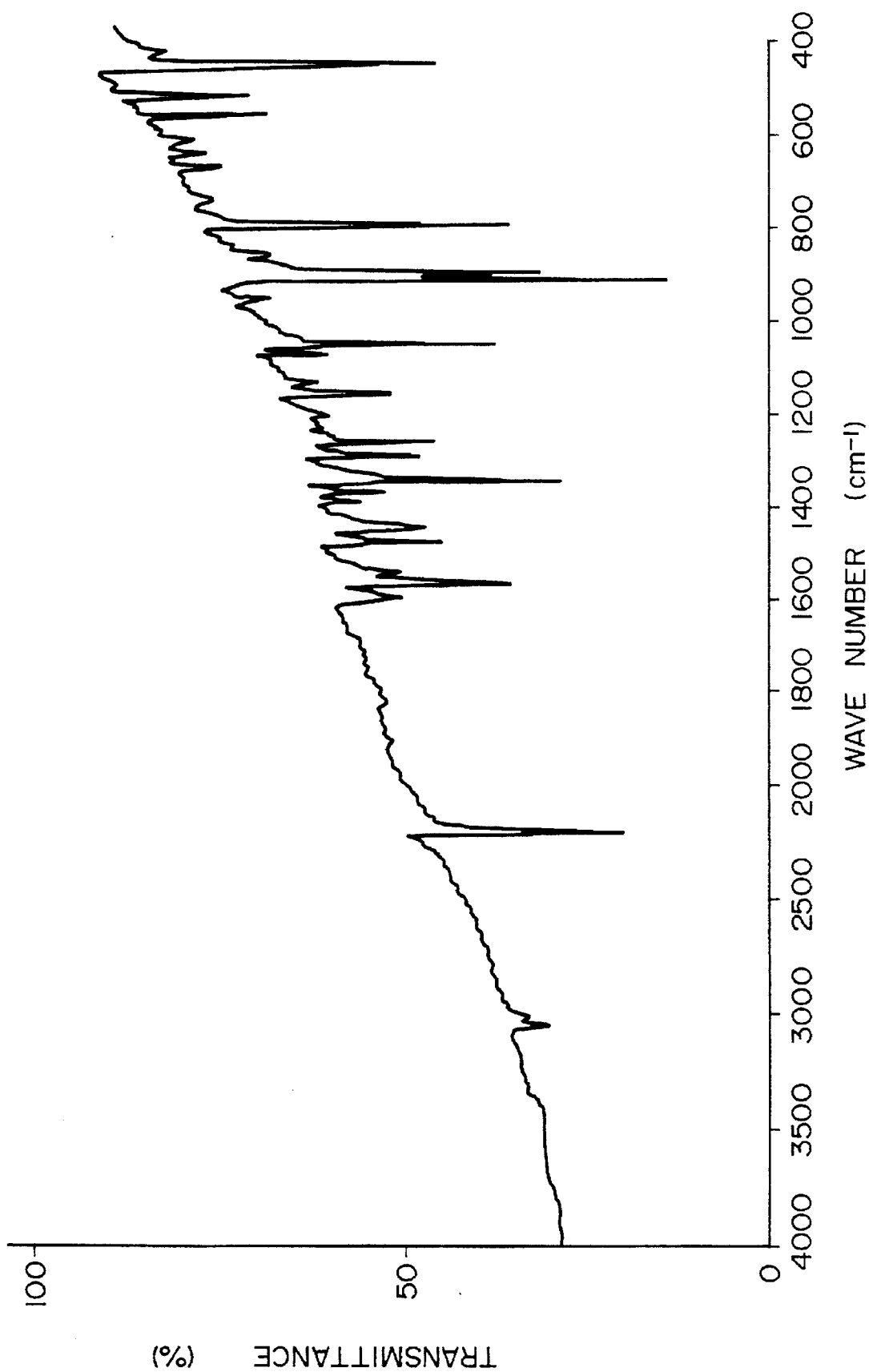
FIG. 3 is an IR spectrum (KBr) of 6-bromo-2,3-dicyanonaphthalene.

(4) IR spectrum (KBr) is shown in FIG. 3.

SYNTHETIC EXAMPLE 3

Synthesis of 6-bromo-1,3-diiminobenz[f]isoindoline

Figure 4:
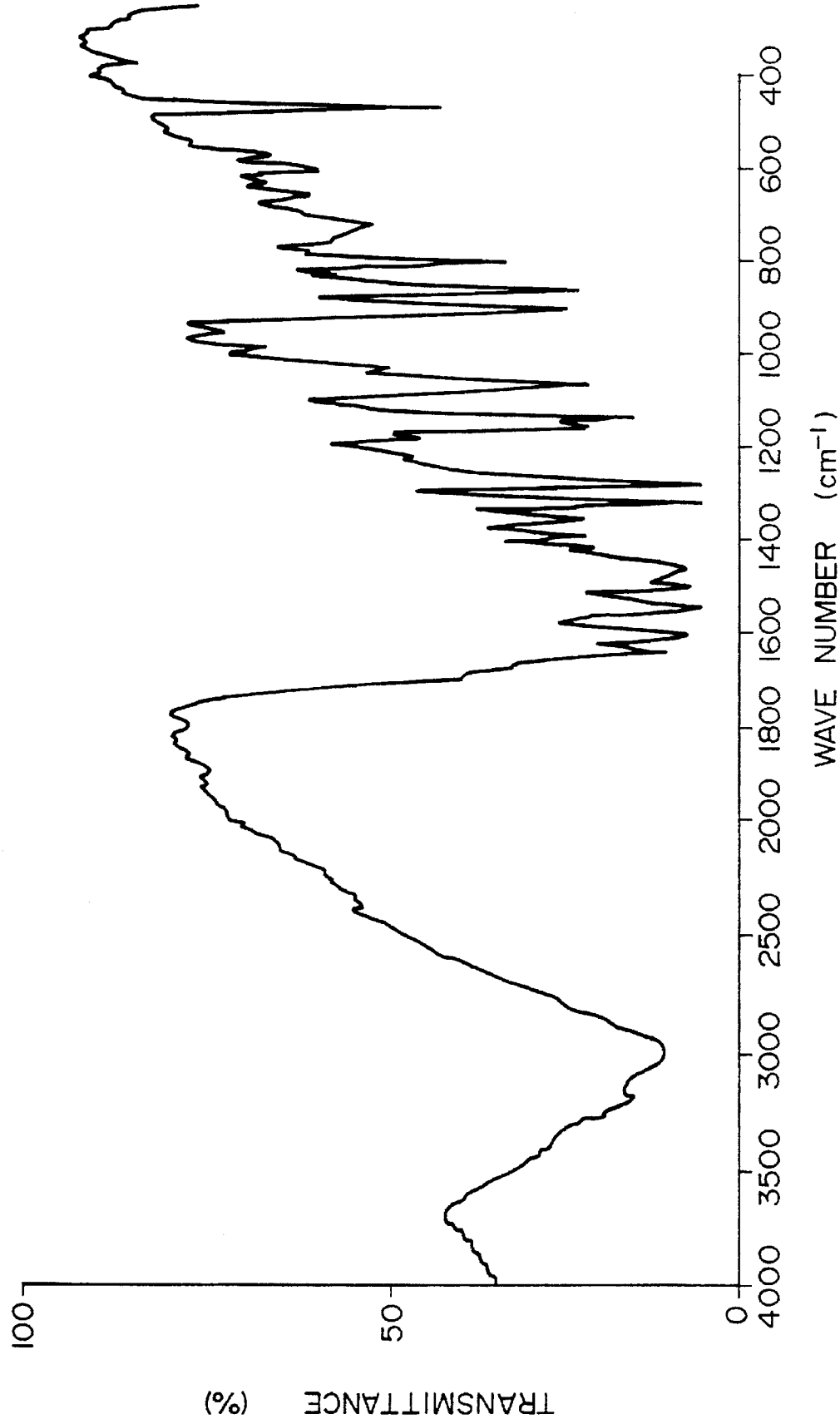
FIG. 4 is an IR spectrum (KBr) of 6-bromo-1,3-diiminobenz[f]isoindoline.

Under nitrogen, 44.1 g (0.17 mol) of 6-bromo-2,3-dicyanonaphthalene was added to a solution of sodium methoxide in methanol prepared by adding 1.92 g (84 mmols) of metallic sodium to 270 ml of absolute methanol in 5 times, and anhydrous ammonia gas was slowly bubbled into the resulting mixture with sufficient stirring at room temperature for about 1 hour. The mixture was refluxed for about 3 hours while bubbling therethrough anhydrous ammonia gas. After cooling, the yellow solid precipitated was filtered and the residue was sufficiently washed with methanol and dried under reduced pressure to obtain 45 g of 6-bromo-1,3-diiminobenz[f]isoindoline as a yellow solid. IR spectrum of this 6-bromo-1,3-diiminobenz[f]isoindoline is shown in FIG. 4. The 6-bromo-1,3-diiminobenz[f]isoindoline was used in the subsequent reaction without further purification.

SYNTHETIC EXAMPLE 4

Synthesis of dichlorosilicon-tetrabromonaphthalocyanine

Under nitrogen, 54 ml of anhydrous tri-n-butylamine was added to a suspension of 22.5 g (81.8 mmols) of 6-bromo-1,3-diiminobenz[f]isoindoline in 110 ml of anhydrous tetralin, followed by adding thereto 14.4 ml (0.126 mol) of silicon tetrachloride, and the resulting mixture was refluxed for about 3 hours. After cooling, 700 ml of methanol was added and the resulting mixture was allowed to stand overnight. The reddish-brown reaction mixture was filtered and the residue was sufficiently washed with methanol and then dried under reduced pressure to obtain about 20 g of dichlorosilicon-tetrabromonaphthalocyanine as a dark-green solid.

Figure 5:
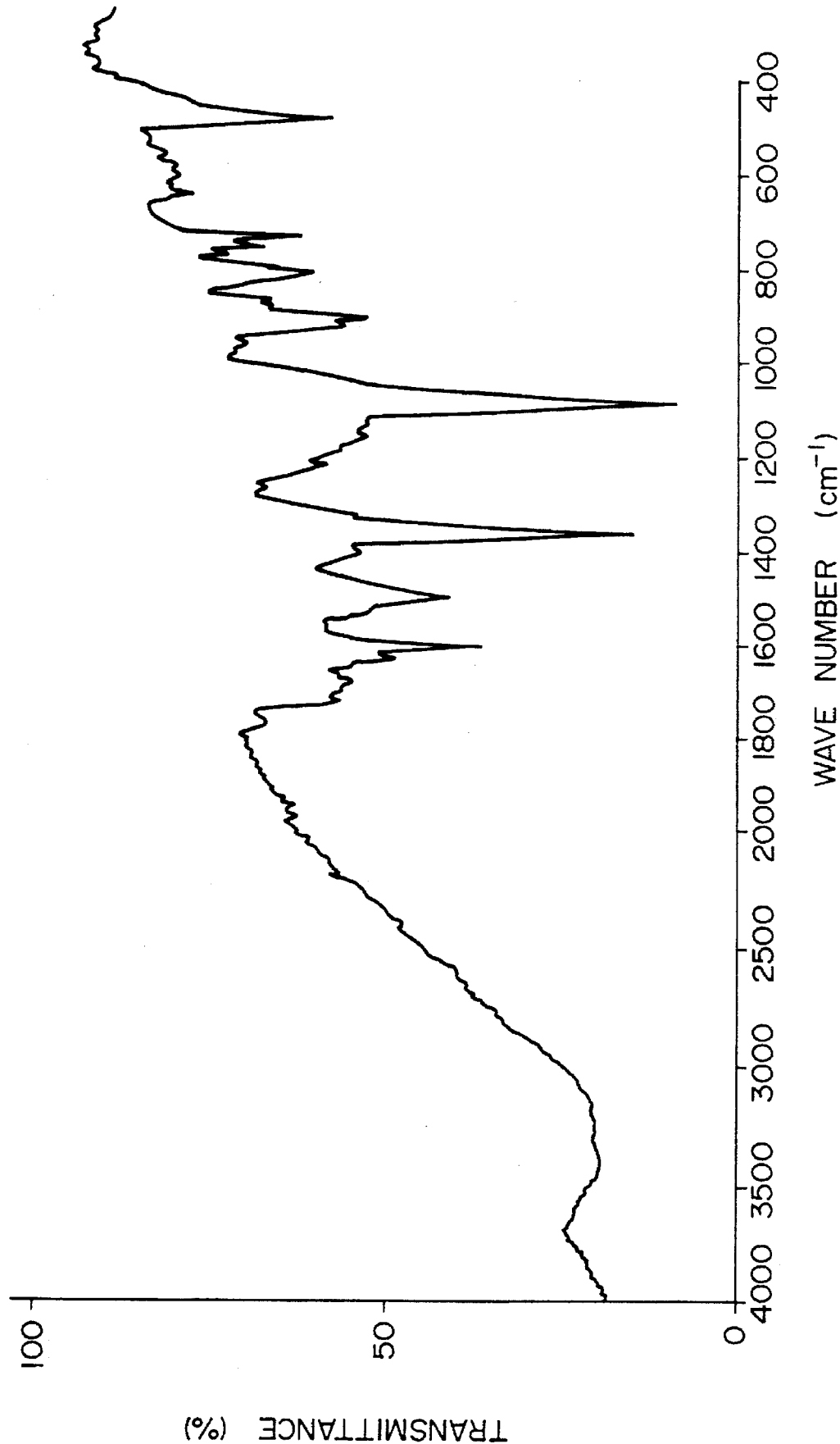
FIG. 5 is an IR spectrum (KBr) of dichlorosilicon-tetrabromonaphthalocyanine.
Figure 6:
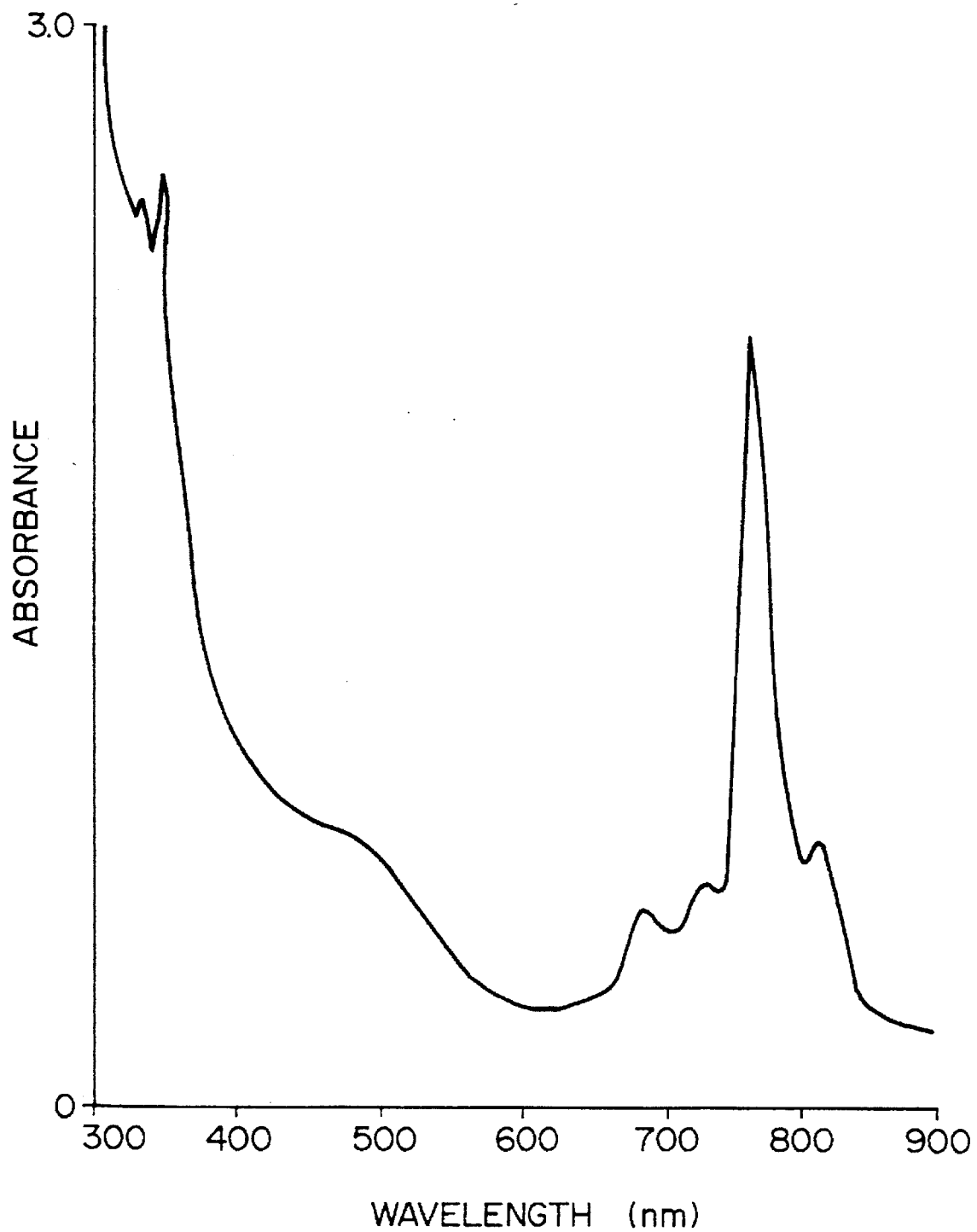
FIG. 6 is an electronic spectrum (tetrahydrofuran solution) of dichlorosilicon-tetrabromonaphthalocyanine.

This dichlorosilicon-tetrabromonaphthalocyanine was used in the subsequent reaction without further purification. IR spectrum of dichlorosilicon-tetrabromonaphthalocyanine is shown in FIG. 5. Its electronic spectrum is shown in FIG. 6.

SYNTHETIC EXAMPLE 5

Synthesis of dihydroxysilicon-tetrabromonaphthalocyanine

Figure 7:
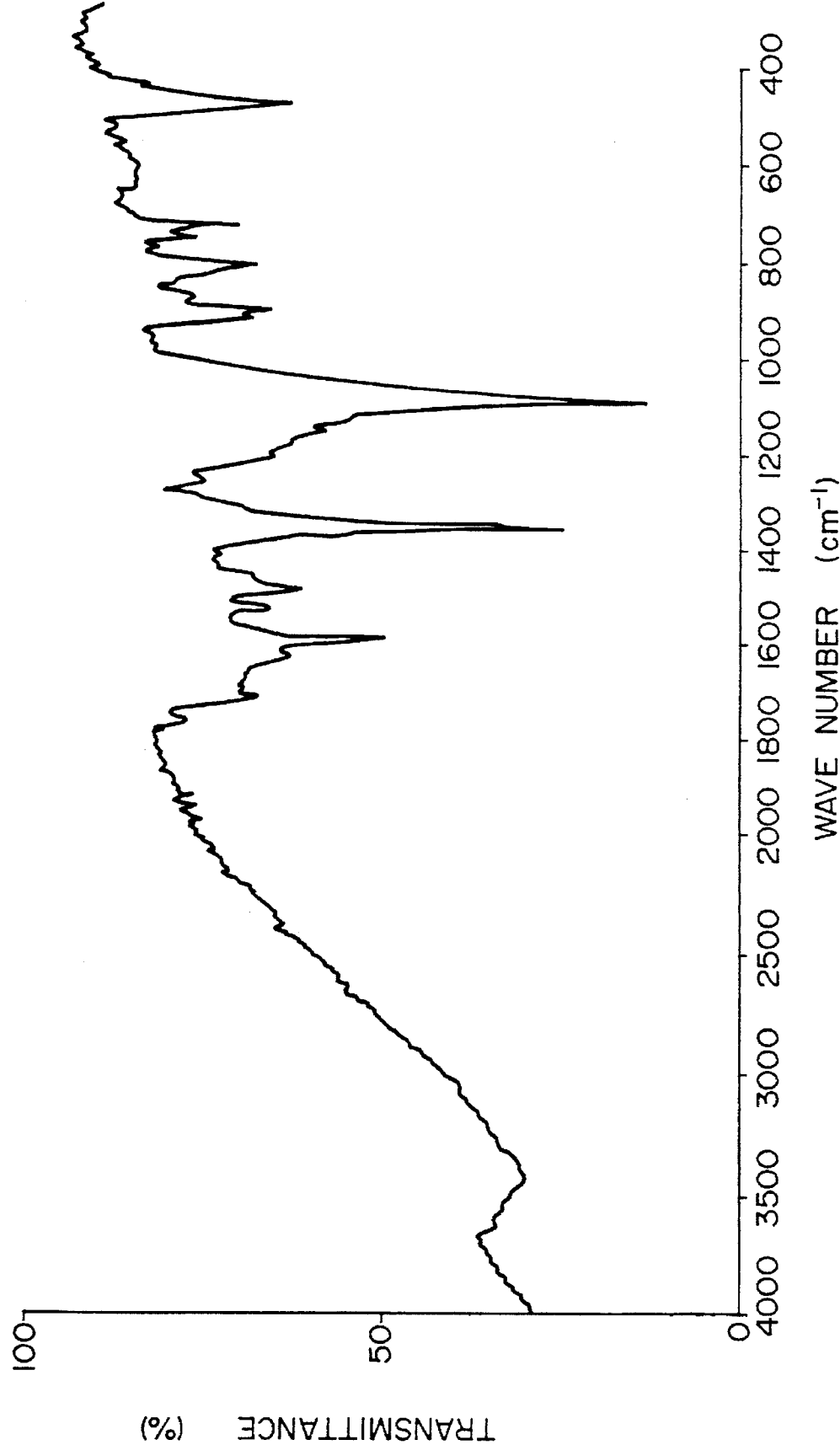
FIG. 7 is an IR spectrum (KBr) of dihydroxysilicon-tetrabromonaphthalocyanine.
Figure 8:
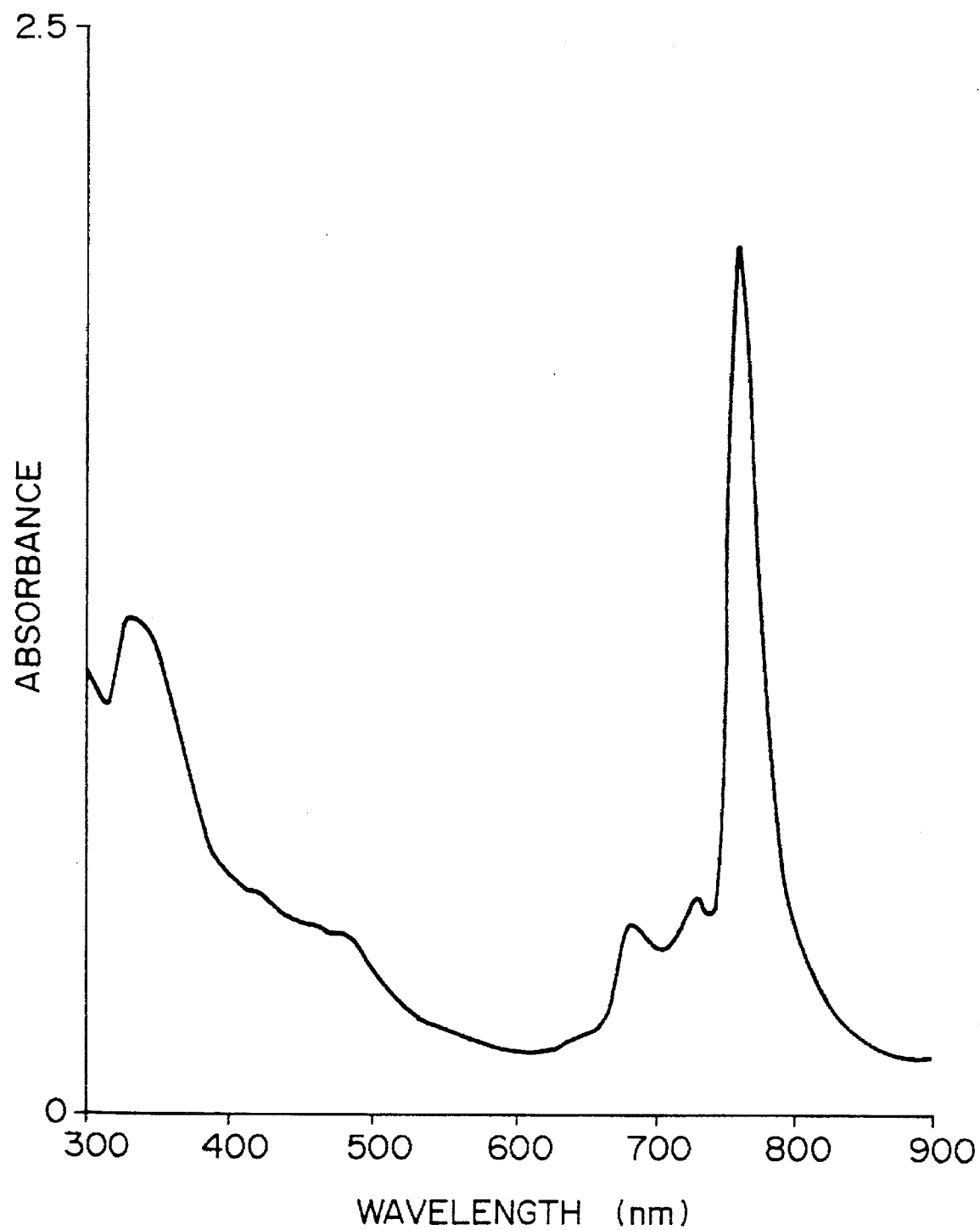
FIG. 8 is an electronic spectrum (tetrahydrofuran solution) of dihydroxysilicon-tetrabromonaphthalocyanine.

To 250 ml of concentrated sulfuric acid was 5 added 9.7 g (8.6 mmols) of dichlorosilicon-tetrabromonaphthalocyanine, and stirred for about 2 hours. The reaction mixture was poured onto about 800 g of ice and the rusulting mixture was allowed to stand overnight. The precipitate formed was filtered, and after sufficient washing with water and then methanol, the precipitate was refluxed in 180 ml of concentrated aqueous ammonia for about 1 hour. After cooling followed by suction filtration, the residue was sufficiently washed successively with water, methanol and acetone, and dried under reduced pressure to obtain 8.7 g of dihydroxysilicon-tetrabromonaphthalocyanine as a dark-green solid. This dihydroxysilicon-tetrabromonaphthalocyanine was used in the subsequent reaction without further purification. IR spectrum of dihydroxysilicon-tetrabromonaphthalocyanine is shown in FIG. 7. Its electronic spectrum is shown in FIG. 8.

SYNTHETIC EXAMPLE 6

Figure 9:
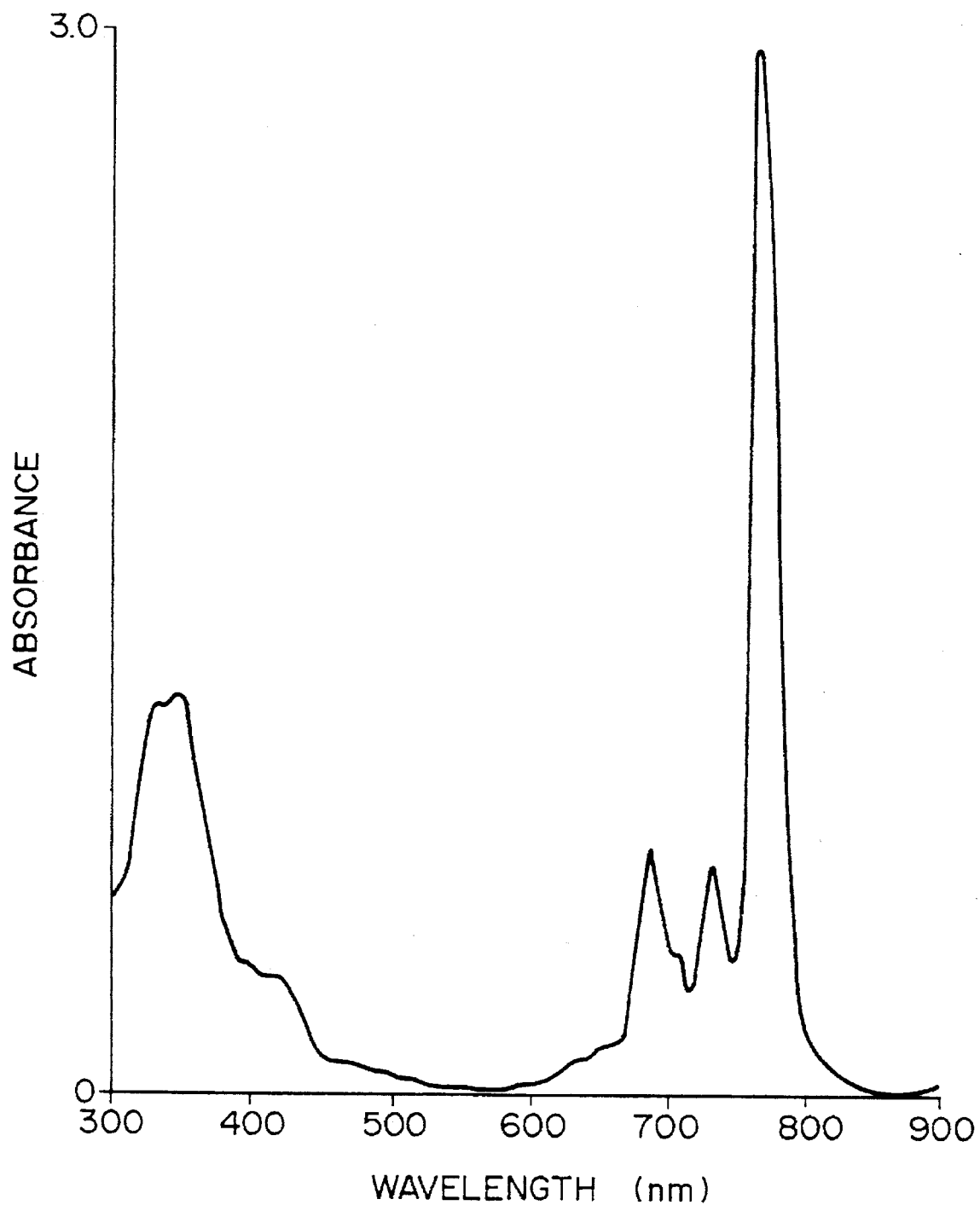
FIG. 9 is an electronic spectrum (methanol solution) of bis(methoxy-polyethylene glycol (Mw about 2,000))-modified silicon-tetrabromonaphthalocyanine.

Synthesis of bis(methoxy-polyethylene glycol (Mw about 2,000))-modified silicon-tetrabromonaphthalocyanine A mixture of 22 mg (0.02 mmol) of dihydroxysilicon-tetrabromonaphthalocyanine, 40 mg (0.02 mmol) of a poly(ethylene glycol) monomethyl ether (Mw about 2,000) and 4 mg (0.02 mmol) of lauric acid was slowly heated to 220° C. with stirring and maintained at 220° C. for 2 hours. After cooling, the reaction product was separated and purified by a molecular sieve column chromatography to obtain 69 mg (68%) of bis(methoxypolyethylene glycol (Mw about 2,000))-modified silicon-tetrabromonaphthalocyanine as a dark-green solid. Electronic spectrum (methanol solution) of this compound is shown in FIG. 9.

SYNTHETIC EXAMPLE 7

Synthesis of bis(methoxy-polyethylene glycol (Mw about 2,000)—NH—$CH_2)_3$—$Si(CH_3)_2$—O)-modified silicon-tetrabromonaphthalocyanine To a solution of 174 mg (0.16 mmol) of dihydroxysilicon-tetrabromonaphthalocyanine and 48 mg (0.7 mmol) of imidazole in 1 ml of anhydrous N,N-dimethylformamide was added dropwise 120 mg (0.7 mmol) of (3-chloropropyl)dimethylchlorosilane with stirring at 20° C. The resulting mixture was stirred at 20° C. for 20 hours, after which the solvent was removed under reduced pressure. By separation and purification from the residue by a silica gel column chromatography, 84 mg (41%) of bis(3-chloropropyldimethylsiloxy)silicon-tetrabromonaphthalocyanine was obtained.

Figure 10:
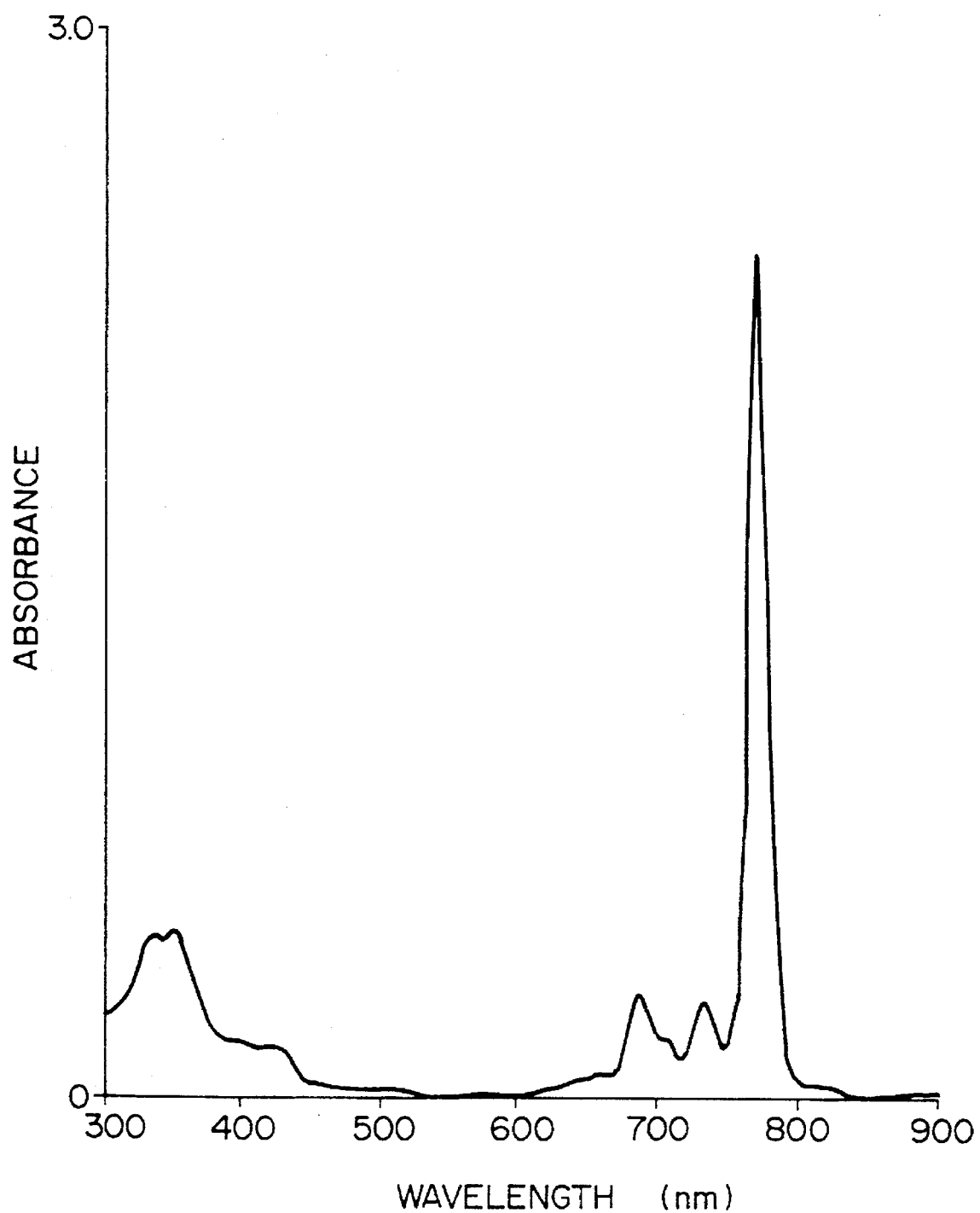
FIG. 10 is an electronic spectrum (methanol solution) of bis(methoxy-polyethylene glycol (Mw about 2,000))—NH—$(CH_2)_3$—$Si(CH_3)_2$—O)-modified silicon-tetrabromonaphthalocyanine.

After a solution of 13 mg (0.01 mmol) of the obtained bis(3-chloropropyldimethylsiloxy)silicon-tetrabromonaphthalocyanine, 400 mg (0.2 mmol) of a terminally aminated poly(ethylene glycol monomethyl ether) (Mw about 2,000) and 1.5 mg (0.01 mmol) of sodium iodide in 1 ml of N,N-dimethylformamide was stirred at 90° C. for 15 hours. Then, the solvent was distilled off under reduced pressure and the reaction product was separated and purified by chromatography in the same manner as described in Synthetic Example 6 to obtain 38 mg (73%) of bis(methoxy-polyethylene glycol (Mw about 2,000)—NH—$(CH_2)_3$—$Si(CH_3)_2$—O)-modified silicon-tetrabromonaphthalocyanine. Electronic spectrum (methanol solution) of this compound is shown in FIG. 10.

SYNTHETIC EXAMPLE 8

Synthesis of bis(methoxy-polyethylene glycol (Mw about 2,000)—NH—CO—NH—$(CH_2)_3$—$Si(CH_3)_2$—O)-modified silicon-tetrabromonaphthalocyanine To a solution of 174 mg (0.16 mmol) of dihydroxysilicon-tetrabromonaphthalocyanine and 150 mg (2.2 mmol) of imidazole in 2 ml of N,N-dimethylformamide was added dropwise 124 mg (0.7 mmol) of 3-isocyanatopropyldimethylchlorosilane with stirring over a period of 1 minute. The stirring was continued at room temperature for 30 hours, after which the solvent was distilled off under reduced pressure to obtain a solid residue.

Figure 11:
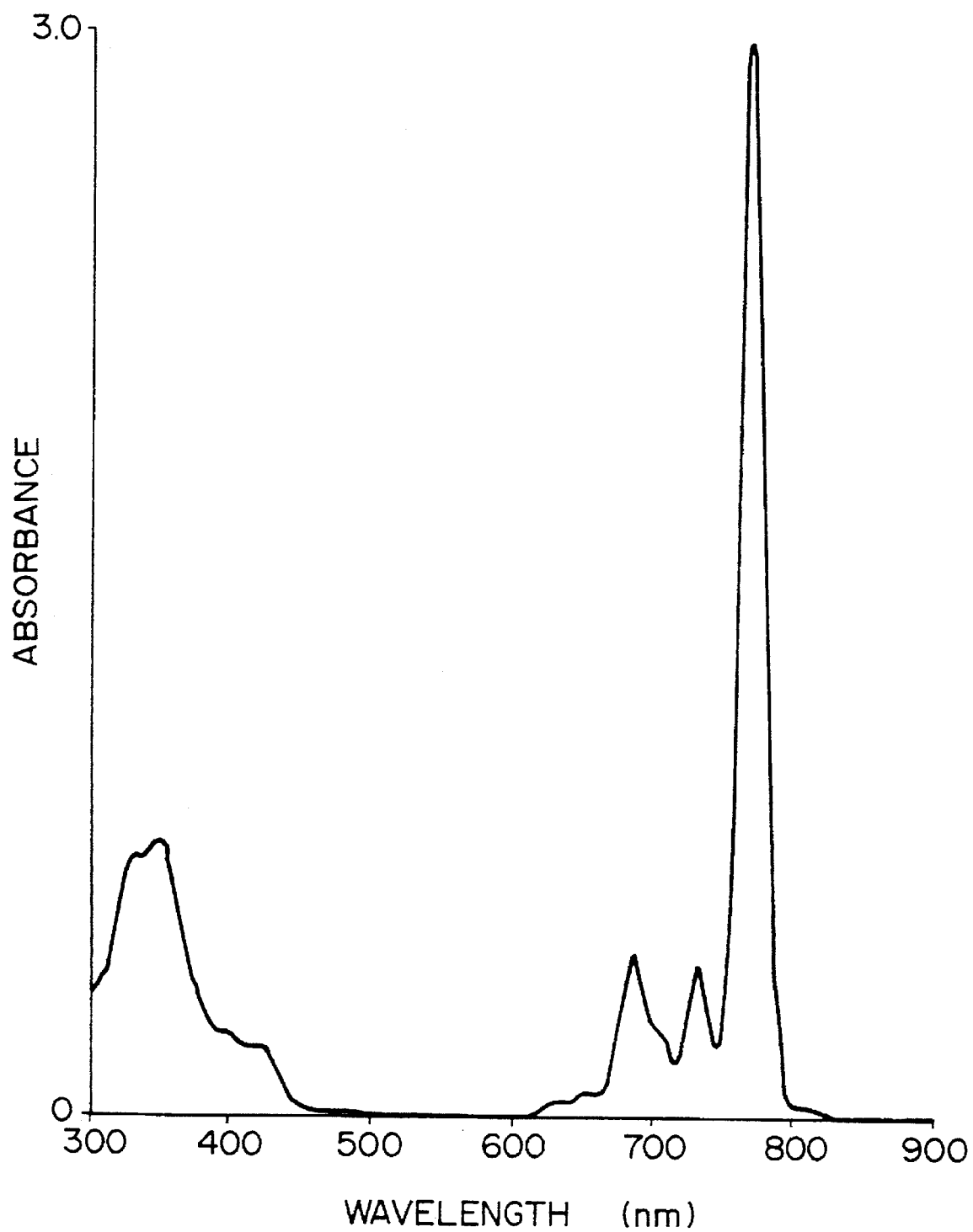
FIG. 11 is an electronic spectrum (methanol solution) of bis(methoxy-polyethylene glycol (Mw about 2,000))—NH—CO.NH—$(CH_2)_3Si(CH_3)_2$—O)-modified silicon-tetrabromonaphthalocyanine.

A solution of 10 mg of the solid obtained and 50 mg (0.025 mmol) of a terminally aminated poly(ethylene glycol) monomethyl ether (Mw about 2,000) in 3 ml of methanol was refluxed for 1 hour. After the solvent was distilled off, the reaction product was separated and purified by reverse phase chromatography (eluent: methanol) to obtain 26 mg of bis(methoxypolyethylene glycol (Mw about 2,000)—NH—CO—NH—$(CH_2)_3$—$Si(CH_3)_2$—O)-modified silicon-tetrabromonaphthalocyanine. Electronic spectrum of this compound is shown in FIG. 11.

SYNTHETIC EXAMPLE 9

Synthesis of methyl 3,4-dimethylbenzoate

To 200 ml of methanol was added 47.6 g (0.317 mol) of 3,4-dimethylbenzoic acid, and the resulting mixture was refluxed for about 4 hours in the presence of about 6 ml of concentrated sulfuric acid with continuous extraction of water by use of Molecular Sieves 3A (a drying agent mfd. by Wako Pure Chemical Industries, Ltd.). After cooling, 600 ml of water was added and the resulting mixture was extracted three times with about 200 ml of benzene. The benzene solution thus obtained was washed three times with a saturated aqueous sodium hydrogencarbonate solution and then three times with water, and dried with anhydrous sodium sulfate. The benzene solution thus treated was concentrated and then distilled under reduced pressure to obtain 49.4 g of a colorless liquid at a boiling point of 133°–134° C./30 mmHg. This liquid was confirmed to be methyl 3,4-dimethylbenzoate from the following analysis results:

(1) Elementary analysis values:

TABLE 4

|  | C | H |
| --- | --- | --- |
| Calculated (%) | 73.15 | 7.37 |
| Found (%) | 73.13 | 7.46 |

(2) NMR spectrum values: $CDCl_3$

δ values: 7.81 (1H, br-s), 7.76 (1H, dd, J=7.93, 1.53 Hz), 7.18 (1H, d, J=7.93 Hz), 3.89 (3H, s), 2.30 (6H, s)

Figure 12:
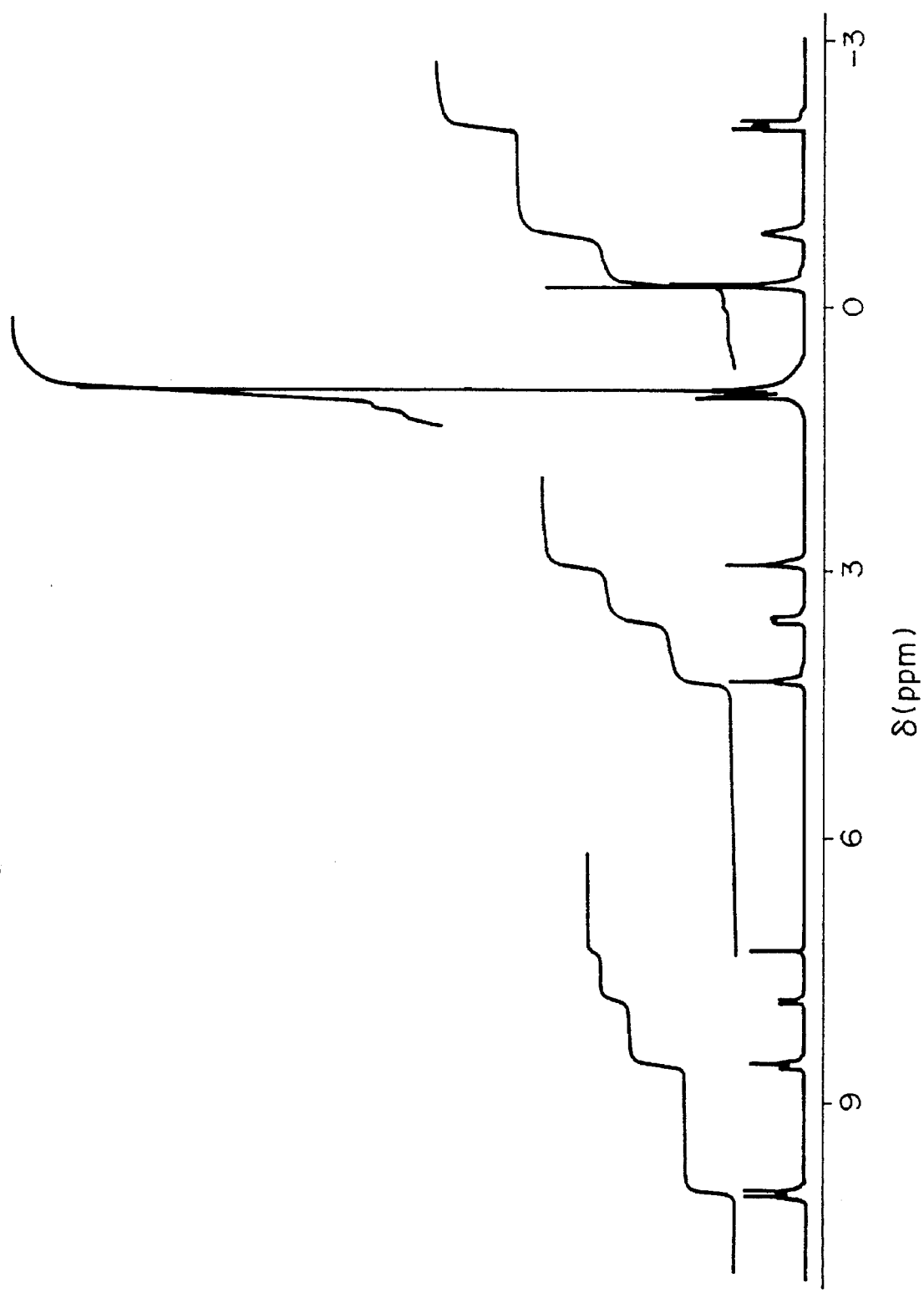
FIG. 12 is an IR spectrum (neat) of methyl 3,4-dimethylbenzoate.

(3) IR spectrum (neat) is shown in FIG. 12.

The spectrum shows an absorption due to ester C=O stretching vibration near 1710 $cm^{-1}$.

SYNTHETIC EXAMPLE 10

Synthesis of 6-methoxycarbonyl-2,3-dicyanonaphthalene

To a solution of 33.8 g (0.2 mol) of methyl 3,4-dimethylbenzoate and 142.2 g (0.8 mol) of N-bromosuccinimide in 500 ml of carbon tetrachloride was added 1 g of benzoyl peroxide, and the resulting mixture was irradiated by a 100-W high pressure mercury arc lamp for 8 to 12 hours under reflux in an irradiating tube. After cooling, the white crystals precipitated were removed by suction filtration and the carbon tetrachloride solution, i.e., the mother liquor was concentrated under reduced pressure. The solid thus obtained was recrystallized from hexane/methylene chloride to obtain 79 g of methyl 3,4-bis(dibromomethyl)benzoate as colorless crystals. Physical properties of methyl 3,4-bis(dibromomethyl)benzoate were as follows:

(1) Melting point: 99.5°–100.5° C.
(2) Elementary analysis values:

TABLE 5

|  | C | H | Br |
| --- | --- | --- | --- |
| Calculated (%) | 25.03 | 1.68 | 66.62 |
| Found (%) | 25.07 | 1.54 | 65.72 |

(3) NMR spectrum values: $CDCl_3$

δ values: 8.29 (1H, br-s), 8.03 (1H, dd, J=8.24, 1.53 Hz), 7.81 (1H, d, J=8.24 Hz), 7.18 (1H, br-s), 7.09 (1H, br-s), 3.96 (3H, s)

Figure 13:
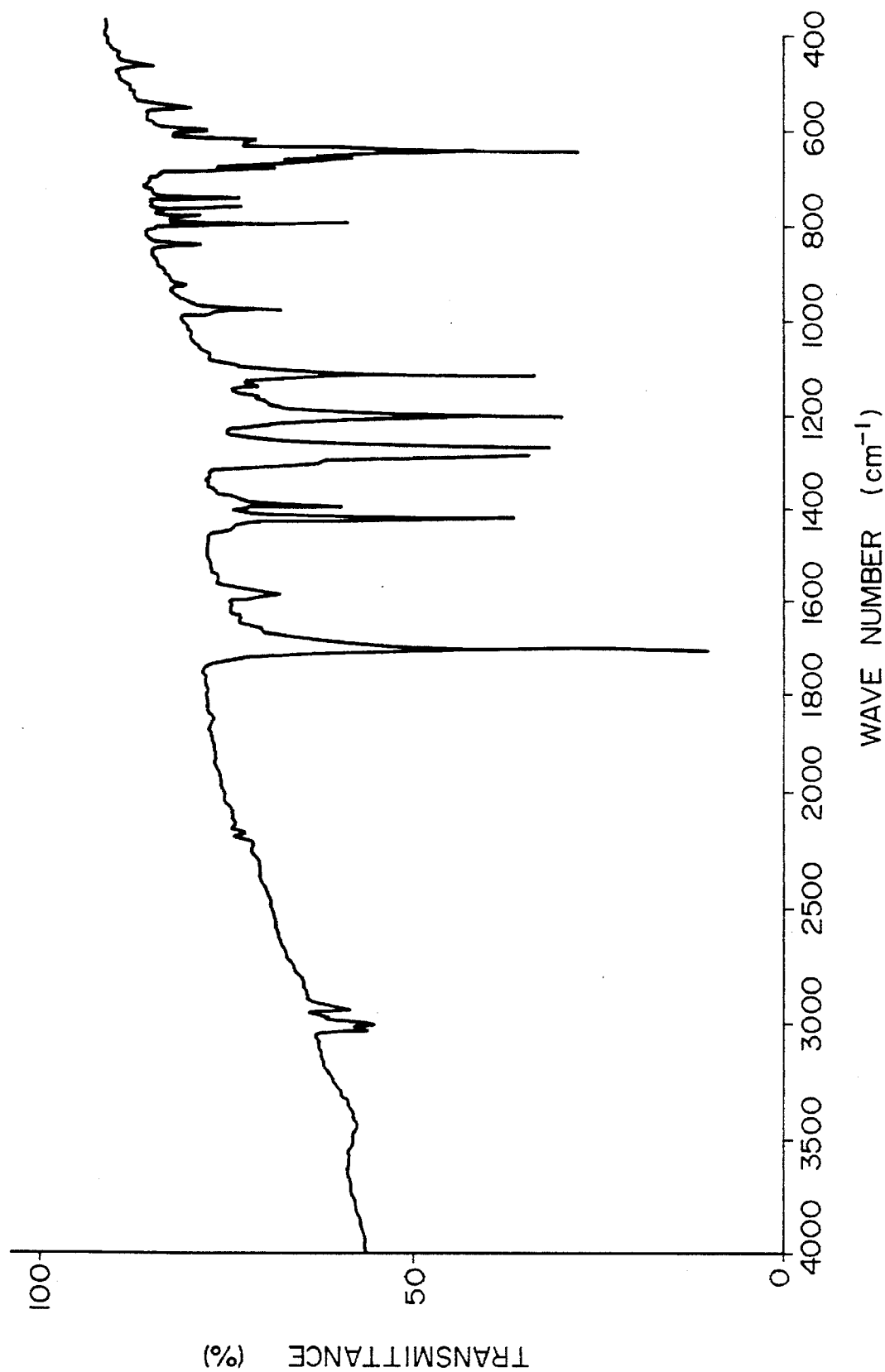
FIG. 13 is an IR spectrum (KBr) of methyl 3,4-bis(dibromomethyl)benzoate.

(4) IR spectrum (KBr) is shown in FIG. 13.

The spectrum shows an absorption due to ester C=O stretching vibration near 1705 $cm^{-1}$.

Next, 100 g (0.67 mol) of sodium iodide was added to a solution of 48 g (0.1 mol) of the methyl 3,4-bis(dibromomethyl)benzoate obtained and 13.5 g (0.173 mol) of fumaronitrile in 400 ml of anhydrous N,N-dimethylformamide with sufficient stirring, and the resulting mixture was stirred under nitrogen at about 75° C. for about 7 hours. After completion of the reaction, the reaction mixture was poured onto about 2 kg of ice. Sodium hydrogensulfite was slowly added until the reddish-brown aqueous solution thus obtained turned light-yellow. Sodium hydrogensulfite was added in a slight excess and after stirring for a while, the resulting mixture was allowed to stand overnight at room temperature. The light-yellow solid precipitated was filtered by suction and sufficiently washed with water and then methanol. The light-yellow solid was recrystallized from acetone/methanol to obtain 13.9 g of colorless needles. The crystals were confirmed to be 6-methoxycarbonyl-2,3-dicyanonaphthalene from the following analysis results:

(1) Melting point: 264°–265° C.
(2) Elementary analysis values:

TABLE 6

|  | C | H | N |
| --- | --- | --- | --- |
| Calculated (%) | 71.18 | 3.41 | 11.86 |
| Found (%) | 71.21 | 3.37 | 11.87 |

(3) NMR spectrum values: $CDCl_3$

δ values: 8.72 (1H, br-s), 8.47 (1H, s), 8.41 (1H, s), 8.38 (1H, dd, J=8.55, 1.53 Hz), 8.06 (1H, d, J=8.55 Hz), 4.04 (3H, s)

Figure 14:
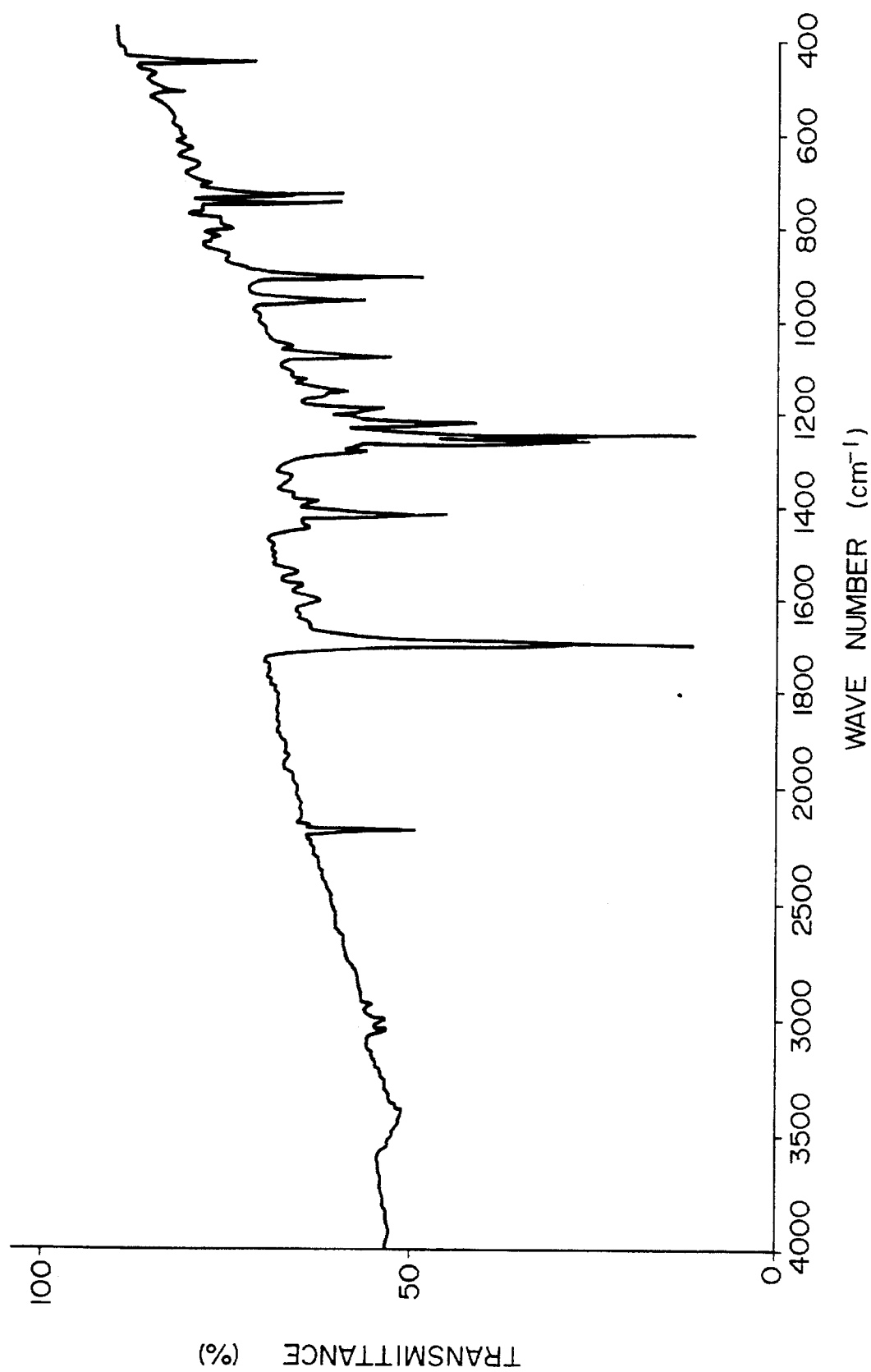
FIG. 14 is an IR spectrum (KBr) of 6-methoxycarbonyl-2,3-dicyanonaphthalene.

(4) IR spectrum (KBr) is shown in FIG. 14.

The spectrum shows an absorption due to ester C=O stretching vibration near 1700 $cm^{-1}$.

SYNTHETIC EXAMPLE 11

Synthesis of 6-chloro-2,3-dicyanoquinoxaline

To 300 ml of ethyl acetate were added 5 g (46.3 mmols) of diaminomaleonitrile, 5 g (41.5 mmols) of anhydrous magnesium sulfate and 15 g (170.3 mmols) of activated manganese dioxide, followed by ultrasonication at about 45° C. for about 30 hours. The reaction mixture was filtered and the filtrate was sufficiently washed with ethyl acetate. The light-yellow mother liquor was concentrated, followed by separation and purification by a silica gel column chromatography (eluent: hexane/ethyl acetate=75/25), whereby 2.90 g (59%) of diiminosuccinonitrile was obtained as colorless crystals.

A mixture of 0.5 g (4.7 mmols) of the diiminosuccinonitrile and 0.67 g (4.7 mmols) of 4-chloro-1,2-phenylenediamine was slowly added to 10 ml of trifluoroacetic acid at about 20° C. over a period of 30 minutes, and the resulting mixture was stirred at room temperature for 8 hours and then allowed to stand overnight. To the reaction mixture was added 50 ml water, and the solid precipitated was filtered and sufficiently washed with water. The solid thus obtained was dried under reduced pressure, followed by a silica gel column chromatography (eluent: hexane/ethyl acetate=75/25) and then recrystallization from chloroform/ethanol, whereby 0.6 g (59%) of 6-chloro-2,3-dicyanoquinoxaline was obtained as colorless crystals.

(1) NMR spectrum values: $CDCl_3$

δ values: 8.28 (1H, d, J=2.13 Hz), 8.23 (1H, d, J=9.16 Hz), 8.04 (1H, dd, J=9.16, 2.13 Hz)

(2) Melting point: 188°–189° C.

Figure 15:
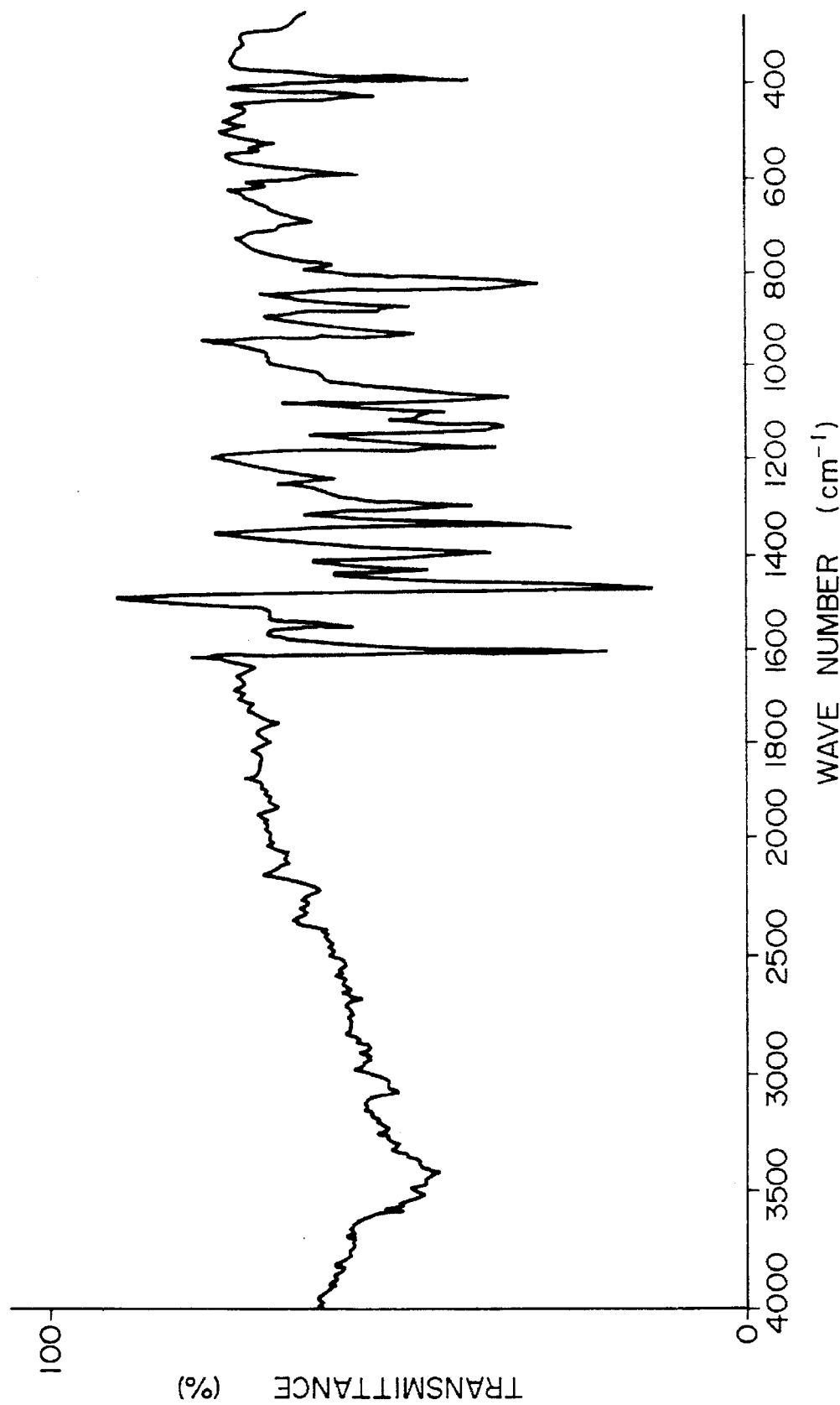
FIG. 15 is an IR spectrum (KBr) of 6-chloro-2,3-dicyanoquinoxaline.

(3) IR spectrum (KBr) is shown in FIG. 15.

SYNTHETIC EXAMPLE 12

Synthesis of dihydroxysilicon-tetrachloroquinoxalocyanine

Under nitrogen, 5.97 g (27.8 mmols) of 6-chloro-2,3-dicyanoquinoxaline was added to a solution of sodium methoxide in methanol prepared by adding 0.12 g (5.4 mmols) of metallic sodium to 75 ml of absolute methanol, and anhydrous ammonia gas was bubbled into the resulting mixture with sufficient stirring at room temperature for about 1 hour. The mixture was refluxed for about 3 hours, while bubbling therethrough anhydrous ammonia gas. After cooling, the reaction mixture was filtered and the residue was sufficiently washed with methanol and dried under reduced pressure to obtain 5.23 g of isoindoline derivative of 6-chloro-2,3-dicyanoquinoxaline as a light-gray solid. The isoindoline derivative was used in the subsequent reaction without further purification.

Under nitrogen, 10 ml (90 mmols) of silicon tetrachloride was added to a suspension of 5.1 g (22.0 mmols) of the above isoindoline derivative in 108 ml of anhydrous quinoline, and the resulting mixture was refluxed for 3 hours. After cooling, the reaction mixture was poured into 300 ml of methanol, and the resulting mixture was allowed to stand overnight at room temperature. The solid precipitated was filtered, sufficiently washed with methanol, and then dried under reduced pressure to obtain a black solid quantitatively. To 100 ml of ethanol were added 6 g of the black solid and then 100 ml of aqueous ammonia, and the resulting mixture was refluxed for about 5 hours.

After cooling, the reaction mixture was filtered and the residue was sufficiently washed with methanol and then dried under reduced pressure to obtain 4.5 g of a black solid. The black solid was considered dihydroxysilicon-tetrachloroquinoxalocyanine and used in the subsequent reaction without further purification.

EXAMPLE 1

Synthesis of sodium bis(methoxy-polyethylene glycol (Mw about 2,000))-modified silicon-naphthalocyaninetetracarboxylate (illustrative compound No. 17)

Figure 16:
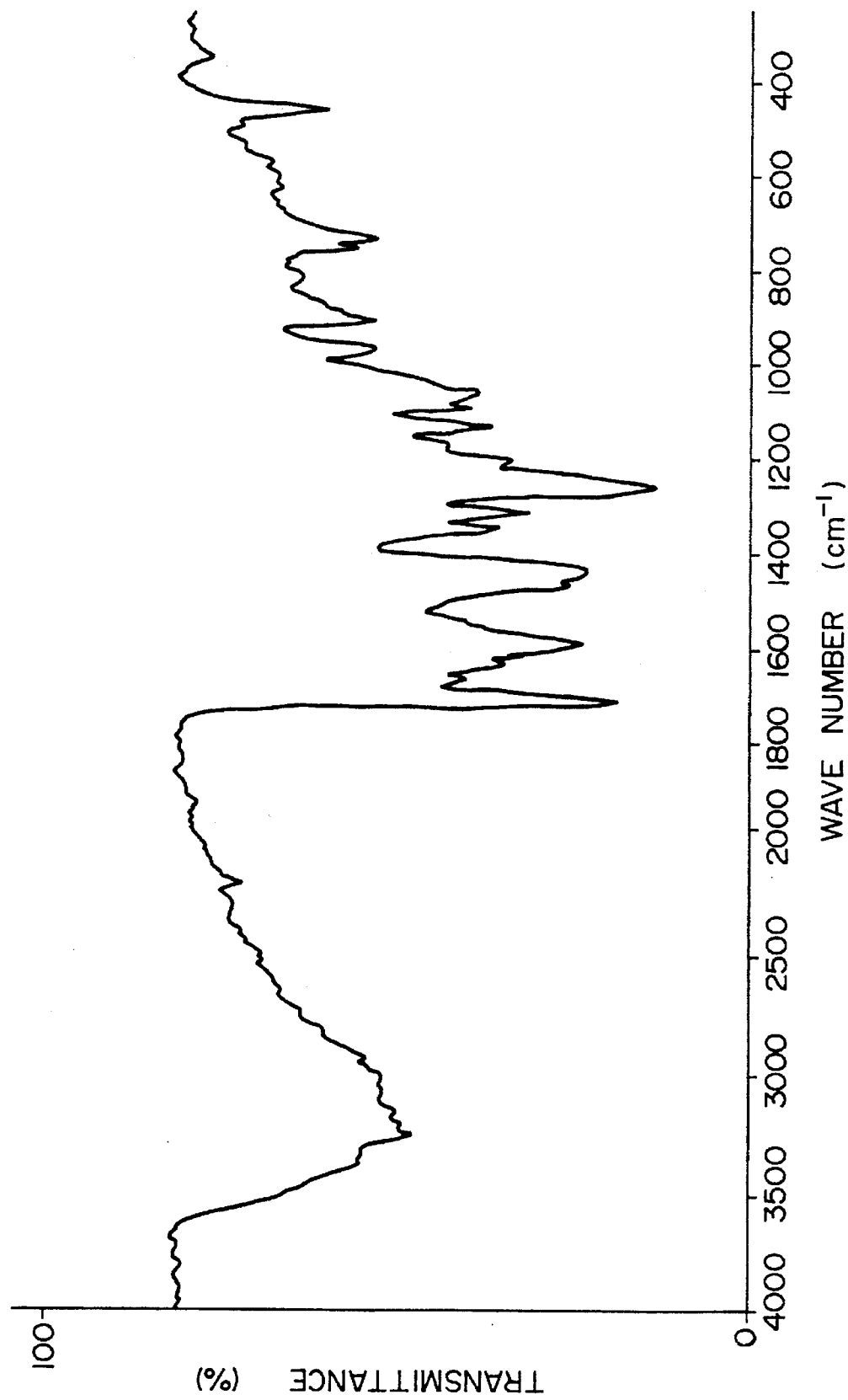
FIG. 16 is an IR spectrum (KBr) of 6-carbamoyl-1,3-diiminobenz[f]isoindoline.

To a solution of sodium methoxide in methanol prepared by adding 0.1 g (4.35 mmols) of metallic sodium to 20 ml of absolute methanol was added 2 g (8.47 mmols) of 6-methoxycarbonyl-2,3-dicyanonaphthalene, and anhydrous ammonia gas was bubbled into the resulting mixture with sufficient stirring at room temperature for about 1 hour. The mixture was refluxed for about 3 hours, while bubbling therethrough anhydrous ammonia gas. After cooling, the yellow solid precipitated was filtered, and the solid was sufficiently washed with methanol and dried under reduced pressure to obtain 1.785 g (88%) of 6-carbamoyl-1,3-diiminobenz[f]isoindoline as a yellow solid. IR spectrum of this 6-carbamoyl-1,3-diiminobenz[f]isoindoline is shown in FIG. 16. The 6-carbamoyl-1,3-diiminobenz[f]isoindoline was used in the subsequent reaction without further purification.

Figure 17:
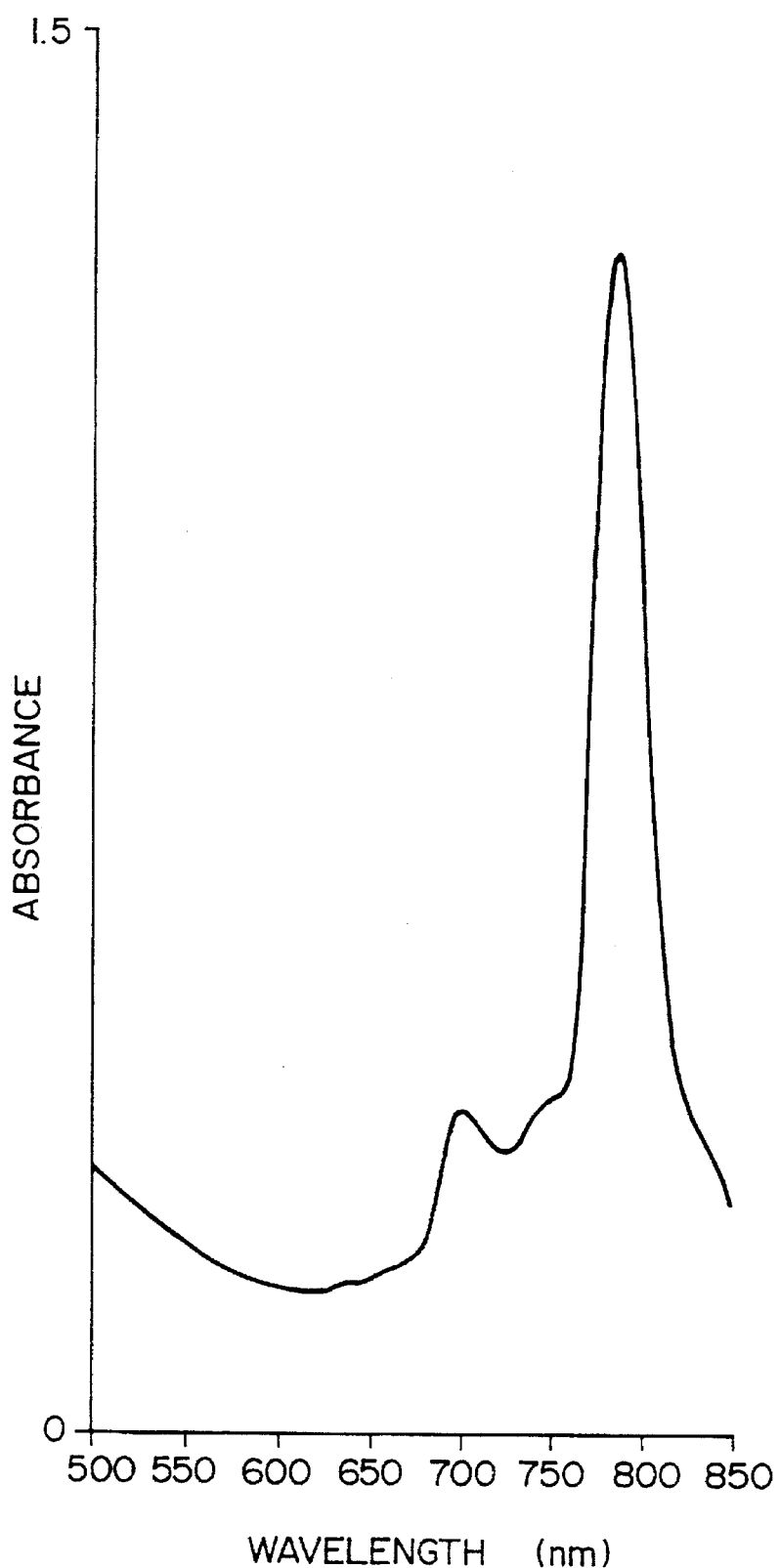
FIG. 17 is an electronic spectrum (quinoline solution) of dihydroxysilicon-tetracarbamoylnaphthalocyanine.

To a suspension of 500 mg (2.10 mmols) of the 6-carbamoyl-1,3-diiminobenz[f]isoindoline in 10 ml of anhydrous quinoline was added 1.8 ml of silicon tetrachloride, and the resulting mixture was stirred at 220° C. for 3 hours. Then, an excess amount of the silicon tetrachloride was distilled off. After cooling, 40 ml of ethanol and 20 ml of concentrated aqueous ammonia were added to the residue, and the resulting mixture was refluxed for 5 hours. After cooling, a dark-green solid thus obtained was filtered and the residue was sufficiently washed with methanol and dried under reduced pressure to obtain 934 mg of a dark-green solid. The dark-green solid was considered to be containing dihydroxysilicon-tetracarbamoylnaphthalocyanine from the electronic spectrum shown in FIG. 17. The dihydroxysilicon-tetracarbamoylnaphthalocyanine was used in the subsequent reaction without further purification.

Figure 18:
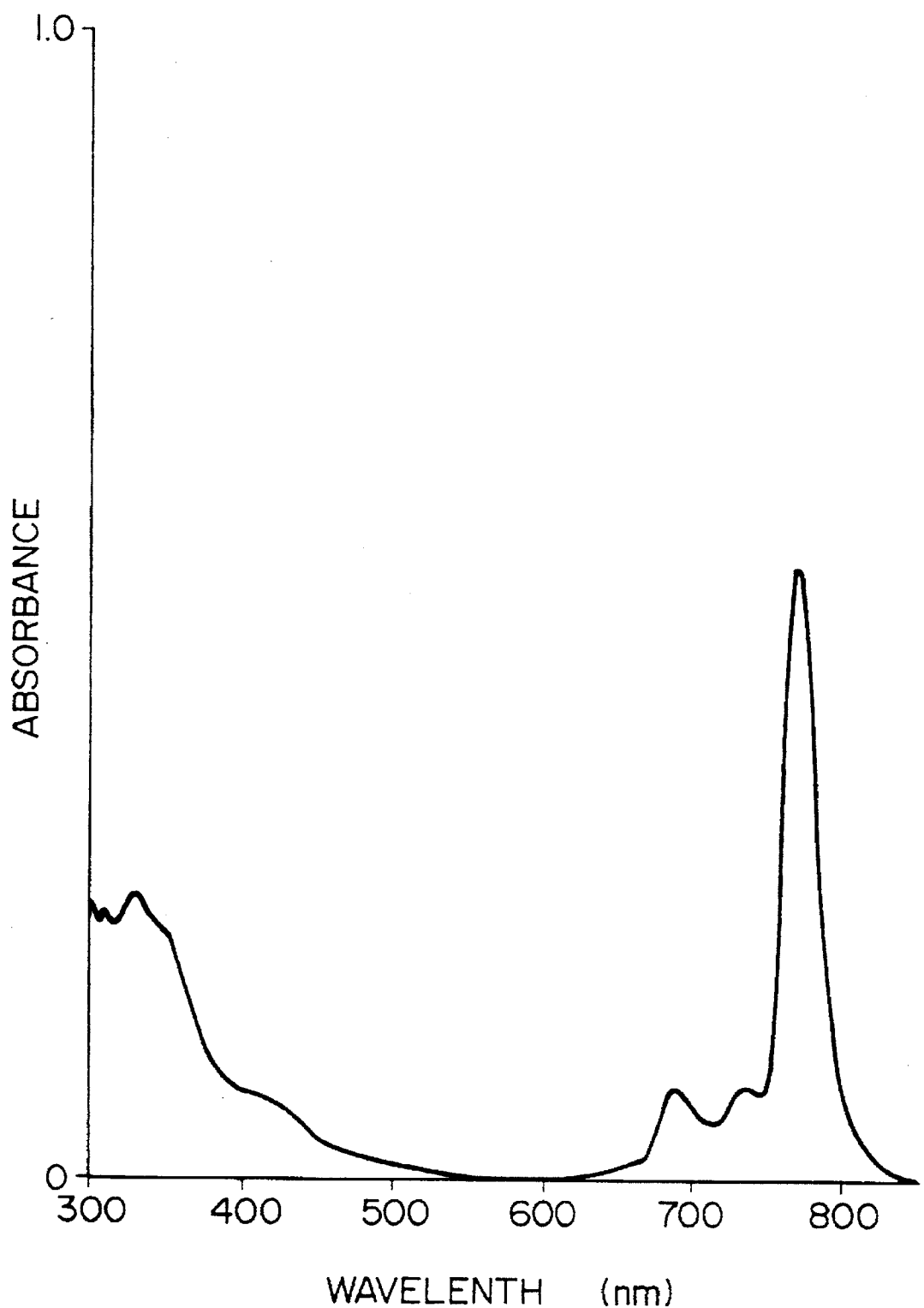
FIG. 18 is an electronic spectrum (methanol solution) of sodium bis(methoxy-polyethylene glycol (Mw about 2,000))-modified silicon-naphthalocyaninetetracarboxylate (illustrative compound No. 17).

A mixture of 19 mg (0.02 mmol) of the dihydroxysilicon-tetracarbamoylnaphthalocyanine, 40 mg (0.02 mmol) of a poly(ethylene glycol) methyl ether (Mw about 2,000) and 4 mg (0.02 mmol) of lauric acid was stirred at 200° C. for 3 hours. After completion of the reaction, 5 ml of 1% aqueous NaOH solution and 10 ml of ethanol were added to the reaction mixture, and the resulting mixture was refluxed for 5 hours. The reaction mixture was filtered while hot and the filtrate was sufficiently washed with methanol and acetone. The mother liquor collected was concentrated, followed by separation and purification by reverse phase chromatography (eluent: methanol), whereby 46 mg of the desired compound sodium bis(methoxy-polyethylene glycol (Mw about 2,000))-modified silicon-naphthalocyaninetetracarboxylate (illustrative compound No. 17) was obtained as a green solid. Electronic spectrum of this compound is shown in FIG. 18.

EXAMPLE 2

Synthesis of sodium bis(methoxy-polyethylene glycol (Mw about 2,000))-modified silicon-tetraphenylthionaphthalocyanineoctacarboxylate (illustrative compound No. 19)

Figure 19:
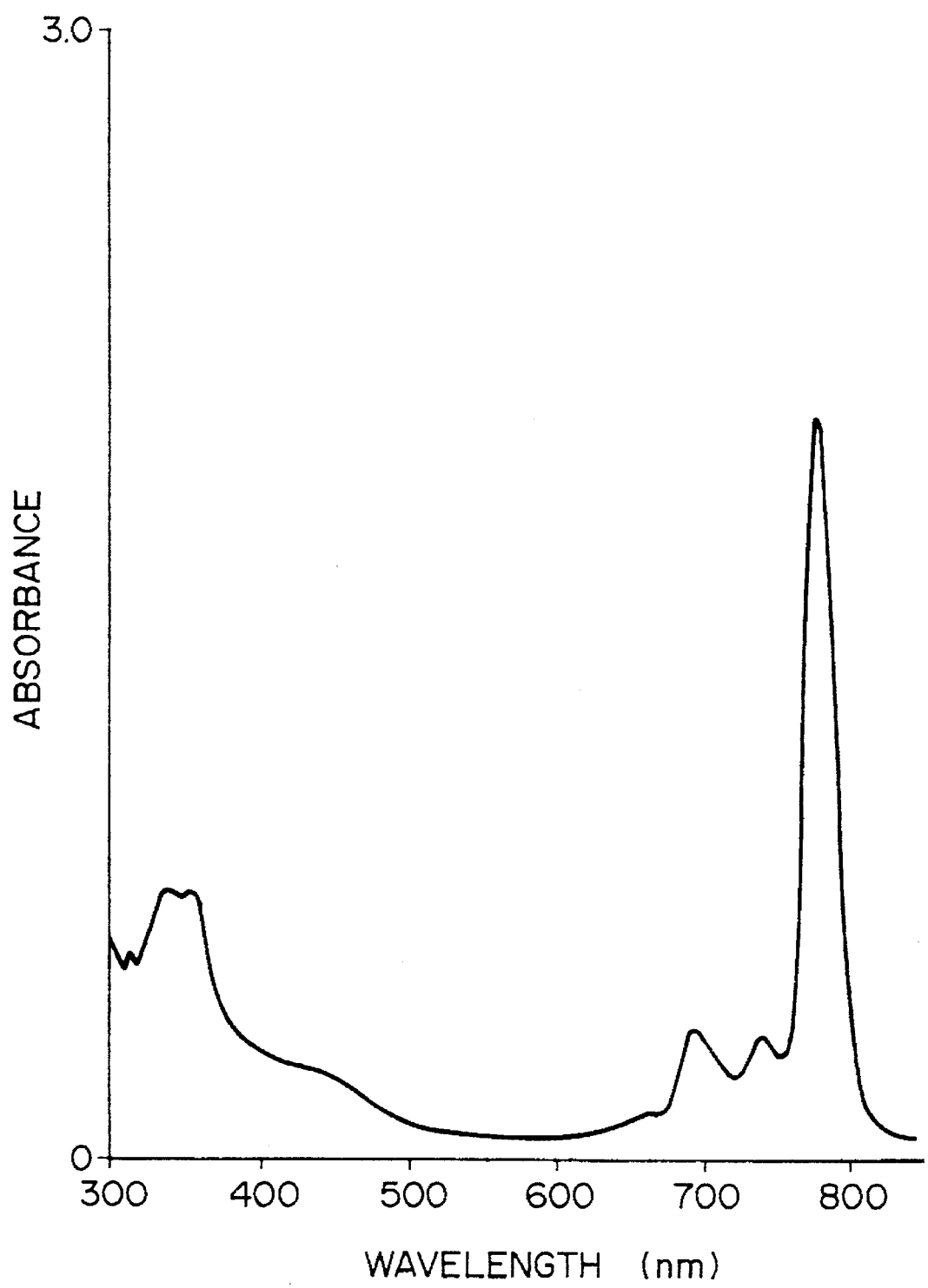
FIG. 19 is an electronic spectrum (methanol solution) of sodium bis(methoxy-polyethylene glycol (Mw about 2,000))-modified silicon-tetraphenylthionaphthalocyanineoctacarboxylate (illustrative compound No. 19).

A suspension of 10 mg (0.002 mmol) of bis(methoxy-polyethylene glycol (Mw about 2,000))-modified silicon-tetrabromonaphthalocyanine and 3 mg (0.009 mmol) of copper(I) 3,5-dimethoxycarbonylphenylthiolate in 1 ml of quinoline was stirred at 140° C. for 15 hours. After completion of the reaction, the reaction mixture was evaporated to dryness under reduced pressure, and 2 ml of a 2% aqueous NaOH solution and 5 ml of ethanol were added to the residue and stirred at 90° C. for 2 hours. After cooling, the reaction mixture was concentrated under reduced pressure and the reaction product was separated and purified by reverse phase chromatography to obtain 8 mg of sodium bis(methoxypolyethylene glycol (Mw about 2,000))-modified silicon-tetraphenylthionaphthalocyanine-octacarboxylate (illustrative compound No. 19) as dark-green crystals. Electronic spectrum (methanol solution) of this compound is shown in FIG. 19.

EXAMPLE 3

Synthesis of sodium bis(methoxy-polyethylene glycol (Mw about 2,000))-modified silicon-tetraphenylthioquinoxalocyanineoctacarboxylate (illustrative compound No. 169)

Figure 20:
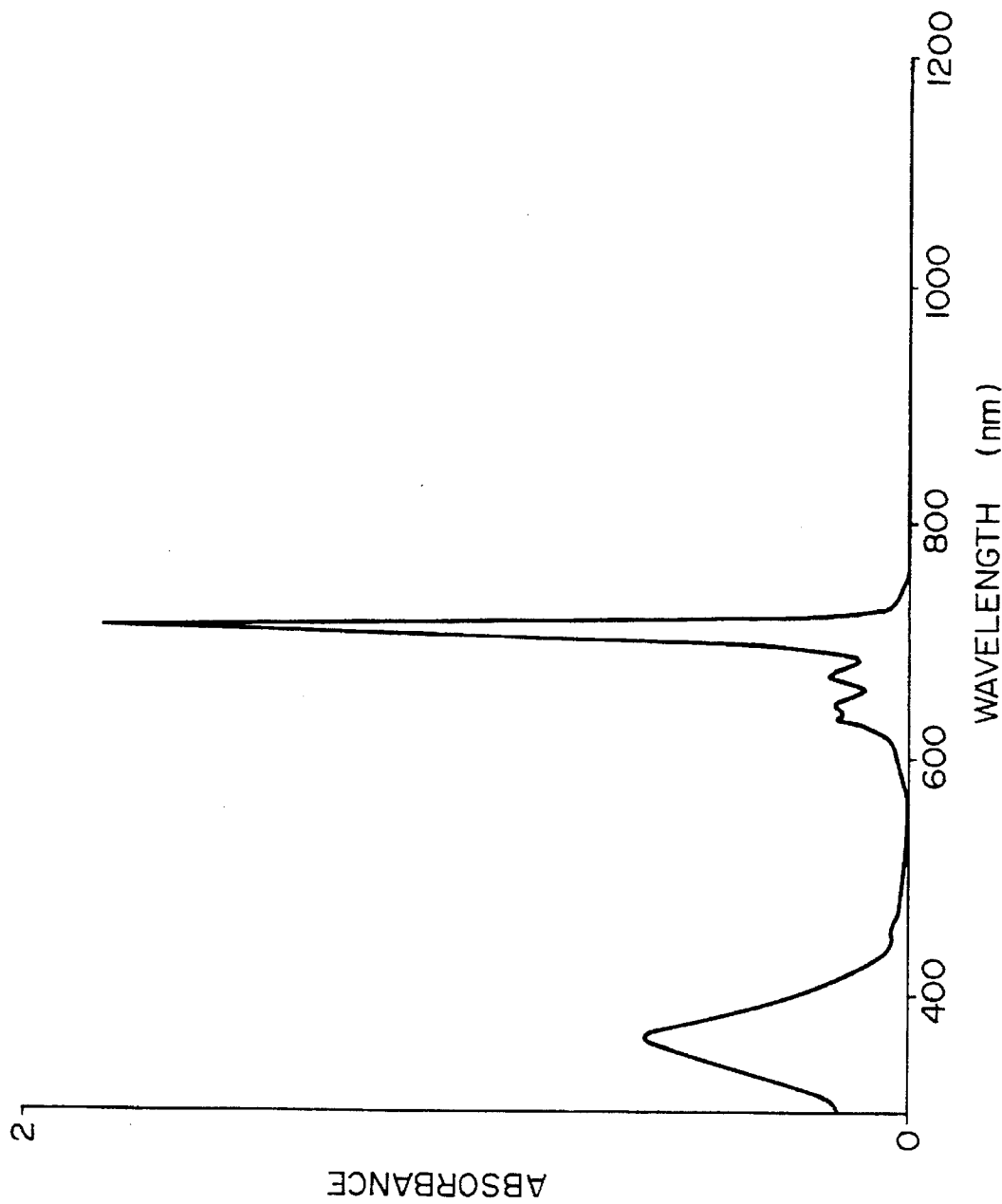
FIG. 20 is an electronic spectrum (methanol solution) of sodium bis(methoxy-polyethylene glycol (Mw about 2,000))-modified silicon-tetraphenylthioquinoxalocyanineoctacarboxylate (illustrative compound No. 169).

A mixture of 18 mg (0.02 mmol) of dihydroxysilicon-tetrachloroquinoxalocyanine, 40 mg (0.02 mmol) of a poly (ethylene glycol) methyl ether (Mw about 2,000) and 4 mg (0.02 mmol) of lauric acid was treated in the same manner as described in Synthetic Example 6 to obtain 58 mg of a dark-green solid. Then, 10 mg (0.002 mmol) of this solid was treated in the same manner as described in Synthetic Example 2 to obtain 4 mg of sodium bis (methoxypolyethylene glycol (Mw about 2,000))-modified silicon-tetraphenylthioquinoxalocyanineoctacarboxylate (illustrative compound No. 169) as dark-green crystals. Electronics pectrum (methanol solution) of this compound is shown in FIG. 20.

EXAMPLE 4

Synthesis of sodium bis(methoxy-polyethylene glycol (Mw about 2,000))-modified silicon-octaphenylthiophenanthracyaninehexadecacarboxylate (illustrative compound No. 79)

A mixture of 32 mg (0.02 mmol) of dihydroxysilicon-octabromophenanthracyanine synthesized by use of 4-bromophenylacetonitrile as starting material according to the method described in a reference (Synthetic Metals, vol. 9, pp. 329–340 (1984)) and Synthetic Examples 3, 4 and 5, 40 mg (0.02 mmol) of a poly(ethylene glycol) methyl ether (Mw about 2,000) and 4 mg (0.02 mmol) of lauric acid, was treated in the same manner as described in Synthetic Example 6 to obtain 72 mg of a dark-green solid. Then, 11 mg (0.002 mmol) of this solid was treated in the same manner as described in Synthetic Example 2 to obtain 5 mg of sodium bis(methoxy-polyethylene glycol (Mw about 2,000))-modified silicon-octaphenylthiophenanthracyaninehexadecacarboxylate (illustrative compound No. 79) as dark-green crystals.

EXAMPLE 5

Synthesis of sodium bis(methoxy-polyethylene glycol (Mw about 2,000))-modified silicon-octaphenylthioanthracyaninehexadecacarboxylate (illustrative compound No. 109)

A mixture of 32 mg (0.02 mmol) of dihydroxysilicon-octabromoanthracyanine synthesized according to the methods described in references (Monatshefte Fur Chemie vol. 117, pp. 745–489 (1986) and J. pract. Chem. vol. 329, pp. S365–373 (1972)) and then Synthetic Examples 3, 4 and 5, 40 mg (0.02 mmol) of a poly(ethylene glycol) methyl ether (Mw about 2,000) and 4 mg (0.02 mmol) of lauric acid, was treated in the same manner as described in Synthetic Example 6 to obtain 65 mg of a dark-green solid. Then, 11 mg (0.002 mmol) of this solid was treated in the same manner as described in Synthetic Example 2 to obtain 4 mg of sodium bis(methoxypolyethylene glycol (Mw about 2,000))-modified silicon-octaphenylthioanthracyaninehexadecacarboxylate (illustrative compound No. 109) as dark-green crystals.

EXAMPLE 6

Synthesis of sodium bis(methoxy-polyethylene glycol (Mw about 2,000))-modified silicon-tetraphenylthio(1,2-naphthalocyanine)octacarboxylate (illustrative compound No. 139)

A mixture of 22 mg (0.02 mmol) of dihydroxysilicon-tetrabromo(1,2-naphtharocyanine) synthesized according to the method described in a references (Chem. Ber., 121, 1479–1486 (1988)) and then Synthetic Examples 3, 4 and 5, 40 mg (0.02 mmol) of a poly(ethylene glycol) methyl ether (Mw about 2,000) and 4 mg (0.02 mmol) of lauric acid, was treated in the same manner as described in Synthetic Example 6 to obtain 51 mg of a dark-green solid. Then, 10 mg (0.002 mmol) of this solid was treated in the same manner as described in Synthetic Example 2 to obtain 6 mg of sodium bis(methoxypolyethylene glycol (Mw about 2,000))-modified silicon-tetraphenylthio(1,2-naphthalocyanine)octacarboxylate (illustrative compound No. 139) as dark-green crystals.

EXAMPLE 7

Synthesis of sodium bis(methoxy-polyethylene glycol (Mw about 2,000))-modified silicon-tetraphenylthioquinolocyanineoctacarboxylate (illustrative compound No. 49)

Figure 21:
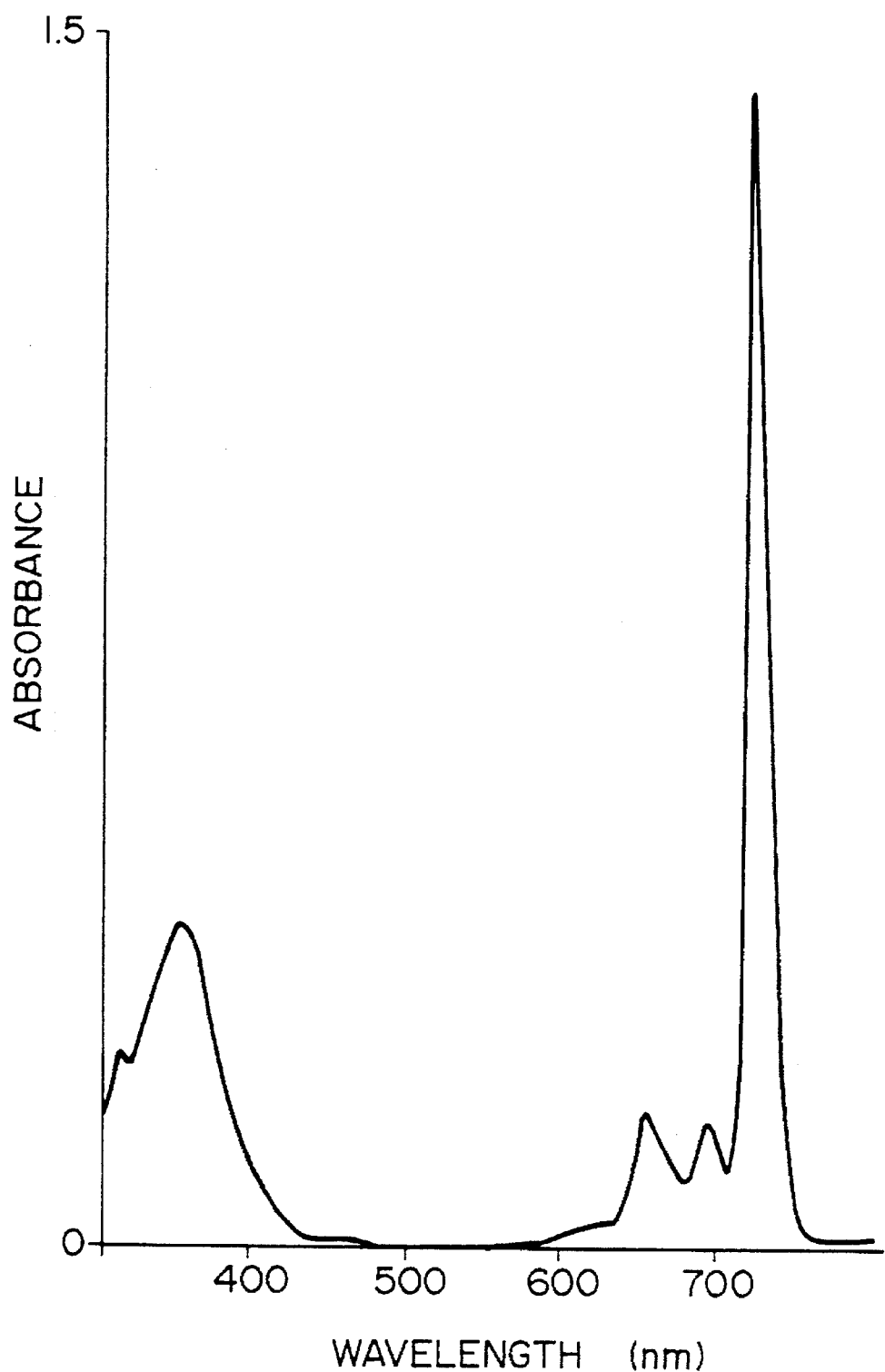
FIG. 21 is an electronic spectrum (methanol solution) of sodium bis(methoxy-polyethylene glycol (Mw about 2,000))-modified silicon-tetraphenylthioquinolocyanineoctacarboxylate (illustrative compound No. 49).

A mixture of 22 mg (0.02 mmol) of dihydroxysilicon-tetrabromoquinolocyanine synthesized according to the methods described in references (U.S. Pat. No. 4,459,409 (1984) and Khim. Geterotsikl, Soedin, pp. 274–278 (1972)) and then Synthetic Examples 3, 4 and 5, 40 mg (0.02 mmol) of a poly(ethylene glycol) methyl ether (Mw about 2,000) and 4 mg (0.02 mmol) of lauric acid, was treated in the same manner as described in Synthetic Example 6 to obtain 32 mg of a dark-green solid. Then, 10 mg (0.002 mmol) of this solid was treated in the same manner as described in Synthetic Example 2 to obtain 5 mg of sodium bis(methoxy-polyethylene glycol (Mw about 2,000))-modified silicon-tetraphenylthioquinolocyanineoctacarboxylate (illustrative compound No. 49) as dark-green crystals. Electronic spectrum (methanol solution) of this compound is shown in FIG. 21.

EXAMPLE 8

Synthesis of sodium bis(methoxy-polyethylene glycol (Mw about 2,000))—NH—$(CH_2)_3$—Si$(CH_3)_2$—O)-modified silicon-tetraphenylthionaphthalocyanineoctacarboxylate (illustrative compound No. 3)

In the same manner as described in Example 2, 11 mg (0.002 mmol) of bis(methoxy-polyethylene glycol (Mw about 2,000))—NH—$(CH_2)_3$—Si$(CH_3)_2$—O)-modified silicon-tetrabromonaphthalocyanine was treated together with 3 mg (0.009 mmol) of copper(I) 3,5-dimethoxycarbonylphenylthiolate to obtain 5 mg of sodium bis(methoxy-polyethyleneglycol (Mw about 2,000))—NH—$(CH_2)_3$—Si$(CH_3)_2$—O)-modified silicon-tetraphenylthionaphthalocyanineoctacarboxylate (illustrative compound No. 3) as dark-green crystals.

EXAMPLE 9

Synthesis of sodium bis(methoxy-polyethylene glycol (Mw about 2,000))—NH—CO.NH$(CH_2)_3$Si$(CH_3)_2$—O)-modified silicon-tetraphenylthionaphthalocyanineoctacarboxylate (illustrative compound No. 7)

In the same manner as described in Example 2, 11 mg (0.002 mmol) of bis(methoxy-polyethylene glycol (Mw about 2,000)—NH—CO.NH$(CH_2)_3$Si$(CH_3)_2$—O)-modified silicon-tetrabromonaphthalocyanine was treated together with 3 mg (0.009 mmol) of copper(I) 3,5-dimethoxycarbonylphenylthiolate to obtain 6 mg of sodium bis(methoxy-polyethylene glycol (Mw about 2,000)—NH—CO.NH$(CH_2)_3$Si$(CH_3)_2$—O)-modified silicon-tetraphenylthionaphthalocyanineoctacarboxylate (illustrative compound No. 7) as dark-green crystals.

TEST EXAMPLE 1

Measurement of Fluorescence Quantum Yield

For the tetraazaporphins of this invention obtained in Examples 1 to 9, fluorescence quantum yield was measured according to the method for measuring relative quantum yield described in a reference [J. Photochem. Photobiol, A. Chemistry, vol. 45, pp. 117–121 (1988)] using 1,1',3,3,3',3'-hexamethylindotricarbocyanine perchlorate or oxazine-720 as a standard substance in the near infrared region. The results obtained are shown in Table 7. As is clear from Table 7, all of the fluorochromes for labeling of this invention show a sufficient fluorescence quantum yield.

TABLE 7

| Compound Example No. | Solvent | Excitation wavelength (nm) | Fluorescence quantum yield |
|---|---|---|---|
| 1 | Methanol | 700 | 0.38 |
| 2 | " | " | 0.39 |
| 3 | " | 650 | 0.55 |
| 4 | " | " | 0.35 |
| 5 | " | 780 | 0.32 |
| 6 | " | 610 | 0.36 |
| 7 | " | 650 | 0.52 |
| 8 | " | 700 | 0.37 |
| 9 | " | " | 0.40 |

EXAMPLE 10 TO 18

Conversion of the Compounds Obtained in Examples 1 to 9 Into Monohydroxypropyl Esters A solution of $4.7 \times 10^{-6}$ mol of each of the compounds obtained in Examples 1 to 9 in 10 ml of methanol was acidified with dilute hydrochloric acid and quickly concentrated to dryness under reduced pressure. Only a material soluble in anhydrous dimethylformamide (DMF) was extracted from the resulting residue with 30 ml of anhydrous DMF, and 0.1 mg ($8.14 \times 10^{-7}$ mol) of N,N-dimethylaminopyridine and 0.35 mg ($4.60 \times 10^{-6}$ mol) of 1,3-propanediol were added to the extract solution, followed by adding thereto 1 mg ($4.85 \times 10^{-6}$ mol) of 1,3-dicyclohexylcarbodiimide (DCC) with sufficient stirring. The stirring was continued at room temperature for 5 hours. To the reaction mixture was added 1 ml of 0.2M $Na_2CO_3$ buffer (pH 9.3), after which the resulting mixture was concentrated under reduced pressure. Separation and purification from the resulting residue by reverse phase chromatography gave monohydroxypropyl ester of the compound. Thus, there were obtained 4 to 6 mg each of monohydroxypropyl esters of the compounds obtained in Examples 1 to 9.

EXAMPLE 19

Synthesis of a Phosphorylated Oligonucleotide Primer

A primer (5'-GTTTCCCAGTCACGAC-3') SEQ ID NO: 1, was synthesized by means of an automatic DNA synthesizer using the solid phase CED-phosphoramide method. The primer synthesized was phosphorylated by incubating the same in 100 μl of a reaction solution containing 50 mM Tris-hydrochloric acid (pH 7.6), 10 mM magnesium chloride, 10 mM dithiothreitol, 3 mMATP and $T_4$-nucleotide kinase, at 37° C. for 1 hour. The primer phosphorylated was separated by a high pressure liquid chromatography (HPLC) using a column for gel filtration. A fraction corresponding to a peak due to the primer phosphorylated was collected, and the solvent was removed by freeze-drying.

EXAMPLES 20 TO 28

To 100 μl of 0.05 mM solution of each of the monohydroxypropyl esters synthesized in Examples 10 to 18 in DMF were added 100 μl of a 0.05 mM solution of the phosphorylated oligonucleotide primer obtained in Example 19 in DMF, and then 100 μl of a 0.05 mM solution of DCC in DMF. The resulting mixture was stirred overnight at room temperature. To the reaction mixture was added 100 μl of a 0.2M $Na_2CO_3$ buffer (pH 9.3), after which the resulting mixture was concentrated under reduced pressure. The reaction product was separated from the resulting residue by HPLC. Thus, products formed by labeling of the oligonucleotide primer with each of the compounds synthesized in Examples 1 to 9 were obtained.

EXAMPLE 29

Analysis of the Base Sequence of DNA

A DNA having a known base sequence was used as a sample. Sanger reaction was carried out for the 4 kinds of bases using each of the primers having a tetraazaporphin attached thereto through a linker synthesized in Examples 20 to 28. The DNA fragments thus obtained were separated by electrophoresis in different lanes for the 4 reaction systems, respectively, and analyzed by means of a DNA sequencer equipped with a semiconductor laser. The results obtained are summarized in Table 8. The reaction systems contained a nonionic surfactant as an additive if necessary.

TABLE 8

| Tetra-azaporphin-labeled primer (tetra-azaporphin Example No.) | Nonionic surfactant | Output wave-length of semi-conductor laser (nm) | Number of bases of DNA | Precision |
|---|---|---|---|---|
| 1 | Triton X-100 | 730 | 380 | 99.7% |
| 2 | " | 780 | 350 | 99.4% |
| 3 | " | 680 | 340 | 99.7% |
| 4 | " | " | 300 | 100% |
| 5 | " | 780 | 350 | 99.7% |
| 6 | " | 680 | 280 | 100% |
| 7 | " | 730 | 320 | 99.4% |
| 8 | " | 780 | 380 | 100% |
| 9 | " | " | 370 | 98.8% |

EXAMPLE 30

Synthesis of tetraazaporphin-labeled primers (labeling compound-ACACAACTGTGTTCACTAGC) SEQ ID NO: 2

Various labeled primers having a 5'-end labeled with a tetraazaporphin (each of the compounds obtained in Examples 1 to 9) (labeling compound-ACACAACTGTGTTCACTAGC SEQ ID NO: 2,) were synthesized in the same manner as described in Example 19 and Examples 20 to 28.

Detection of β-globin gene in human DNA

Human β-globin gene was detected by a gene detection method using the PCR (Polymerase Chain Reaction) method.

SAMPLE 1

Twenty cycles of gene amplification was carried out (the total volume of solution: 100 μl) according to the protocol of Perkin-Elmer-Cetus Corporation by using human placental DNA (1 μg), each of the labeled primers, i.e., labeling compound-ACACAACTGTGTTCACTAGC, SEQ ED NO: 2 synthesized in the manner described above (300 ng), HO-CAACTTCATCCACGTTCACC (300 ng), SEQ ID NO: 3 a nonionic surfactant, and TaqDNA polymerase (Perkin-Elmer-Cetus Corporation).

SAMPLE 2

Human placental DNA (1 μg), the same labeling compound-ACACAACTGTGTTCACTAGC SEQ ID NO: 2, as in sample 1 (300 ng), HO-CAACTTCATCCACGTTCACC SEQ ID NO: 3, (300 ng) and a nonionic surfactant were added to a reaction solution containing no TaqDNA polymerase which had been prepared according to the protocol of Perkin-Elmer-Cetus Corporation (the total volume of the solution: 100 μl).

To each of the samples (50 μl) was added 450 μl of buffer solution A (containing a nonionic surfactant, 50 mM NaCl, 10 mM Tris-HCl and 0.1 mM EDTA, pH 8.0), and the resulting mixture was added to octadecyl silane resin (Micro Bonda Pack C-18, Waters Co.) previously washed with buffer solution A. The octadecylsilane resin used was in the form of a layer formed by layering a suspension of the resin in ethanol over siliconized glass wool packed into the end of a pipet chip (for 1 ml).

After washing with buffer solution A (500 μl) and buffer solution A containing 5% ethanol (500 μl), elution was carried out using buffer solution A containing 10% ethanol (500 μl). The pH of the eluate was adjusted to about 8, and fluorescence intensity was measured by means of a photodiode array by using a semiconductor laser as an exciting light source. Consequently, the relative intensities shown in Table 26 were attained.

Unreacted labeling compound-ACACAACTGTGTTCACTAGC SEQ ID NO: 2 was usually not eluted at all with buffer solution A containing 10% ethanol, and was eluted only with buffer solution A containing 15% ethanol.

From these results, it was found that β-globingene in human DNA can be detected using an oligodeoxy-nucleotide labeled with the tetraazaporphin of this invention at the 5'-end.

TABLE 9

| Example No. | Nonionic surfactant | Output wavelength of semiconductor laser (nm) | Relative intensity Sample 1 | Sample 2 |
|---|---|---|---|---|
| 1 | Tween 20 | 730 | 4 | 183 |
| 2 | " | 780 | 6 | 166 |
| 3 | " | 680 | 2 | 135 |
| 4 | " | " | 7 | 147 |
| 5 | " | 780 | 6 | 153 |
| 6 | " | 680 | 5 | 144 |
| 7 | " | 730 | 4 | 171 |
| 8 | " | 780 | 8 | 158 |
| 9 | " | " | 3 | 159 |

COMPARATIVE EXAMPLE 1

Each of the phthalocyanines disclosed in International Publication Number WO89/03807 was attached to the oligonucleotide primer obtained in Example 19, according to the method of grafted patents and the methods described in Examples 20 to 28 of this invention. Using each of the phthalocyanine-attached oligonucleotides thus obtained, the base sequence of DNA was analyzed in the same manner as in Example 29.

The phthalocyanines used in this experiment are described below.

Comparative-example compound A: aluminum hydroxy-2,9,16,23-tetraphenoxyphthalocyaninesulfonate Comparative-example compound B: aluminum hydroxy-2,9,16,23-tetrathiophenylphthalocyaninesulfonate Comparative-example compound C: magnesium 20-phenyltetrabenztriazaporphinsulfonate Comparative-example compound D: sodium bis (tributylsiloxy)silicon-phthalocyaninetetracarboxylate The results obtained are shown in Table 10.

As shown in Table 10, the phthalocyanines could not be excited by means of a semiconductor laser emitting a wavelength of 730 nm or more, so that no fluorescence was observed at all. Therefore, measurement became impossible. Moreover, when a semiconductor laser emitting a wavelength of 680 nm was used, the precision of measurement was significantly lowered by interference of scattered light.

TABLE 10

| Comparative example compound | Nonionic surfactant | Output wavelength of semiconductor laser (nm) | Number of bases of DNA | Precision |
|---|---|---|---|---|
| A | Triton X-100 | 830 | Not measurable | |
| " | " | 780 | " | |
| " | " | 730 | " | |
| " | " | 680 | 130 | 50% |
| B | " | 830 | Not measurable | |
| " | " | 780 | " | |
| " | " | 730 | " | |
| " | " | 680 | 120 | 48% |
| C | " | 830 | Not measurable | |
| " | " | 780 | " | |
| " | " | 730 | " | |
| " | " | 680 | 140 | 54% |
| D | " | 830 | Not measureable | |
| " | " | 780 | " | |
| " | " | 730 | " | |
| " | " | 680 | " | |

COMPARATIVE EXAMPLE 2

The phthalocyanines of comparative-example compounds A to D were utilized for detecting β-globin gene in human DNA, in the same manner as described in Example 30.

The results obtained are shown in Table 11.

As shown in Table 11, the phthalocyanines could not be excited by means of a semiconductor laser emitting a wavelength of 730 nm or more, so that no fluorescence was observed at all. Therefore, measurement became impossible. Moreover, when a semiconductor laser emitting a wavelength of 680 nm was used, it became difficult to distinguish relative fluorescence intensities between of sample 1 and of sample 2 because of interference of excitation light source.

TABLE 11

| Comparative example compound | Nonionic surfactant | Output wavelength of semi-conductor laser (nm) | Relative intensity Sample 1 | Relative intensity Sample 2 |
|---|---|---|---|---|
| A | Triton X-100 | 830 | Not measurable | Not measurable |
| " | " | 780 | Not measurable | Not measurable |
| " | " | 730 | Not measurable | Not measurable |
| " | " | 680 | 125 | 146 |
| B | " | 830 | Not measurable | Not measurable |
| " | " | 780 | Not measurable | Not measurable |
| " | " | 730 | Not measurable | Not measurable |
| " | " | 680 | 118 | 151 |
| C | " | 830 | Not measurable | Not measurable |
| " | " | 780 | Not measurable | Not measurable |
| " | " | 730 | Not measurable | Not measurable |
| " | " | 680 | 131 | 144 |
| D | " | 830 | Not measurable | Not measurable |
| " | " | 780 | Not measurable | Not measurable |
| " | " | 730 | Not measurable | Not measurable |
| " | " | 680 | Not measurable | Not measurable |

EXAMPLE 31 TO 39

In methanol, 0.13 mmol of each of the tetraazaporphins synthesized in Examples 1 to 9 was acidified with concentrated hydrochloric acid, followed by quick concentration under reduced pressure. Only a material soluble in DMF was extracted from the resulting residue with 20 ml of DMF to obtain a dark-green DMF solution. To this solution was added 18 mg (0.13 mmol) of p-aminobenzoic acid (PABA). With cooling at about 0° C., to the resulting solution were added a solution of 0.02 ml of diethylphosphoryl cyanide (DEPC) in 3 ml of DMF, and then 0.04 ml (0.28 mmol) of triethylamine, and the resulting mixture was stirred at 0° C. for 30 minutes. Then, the stirring was continued at room temperature for 3 hours. After completion of the reaction, 1 ml of water was added to the reaction mixture and the resulting mixture was concentrated under reduced pressure. Separation and purification from the resulting residue by reverse phase chromatography gave a compound formed by the binding of the tetraazaporphin to a molecule of PABA.

Thus, there were obtained compounds formed by the binding of each of the tetraazaporphins synthesized in Examples 1 to 9 to a molecule of PABA.

EXAMPLES 40 TO 48

A solution of each of the compounds obtained in Examples 31 to 39, i.e., tetraazaporphin (synthesized in Examples 1 to 9)-PABA and 3-(4-aminobutyl)morphine in DMF was treated with DEPC in the presence of triethyl amine in the same manner as described in Examples 31 to 39. Thus, tetraazaporphin-PABA-morphine combined products were obtained.

EXAMPLE 49

Measurement of Relative Immuno-affinity for Antimorphine Monoclonal Antibody

For morphine, aminomorphine and the above-mentioned fluorochrome-labeled morphines, relative immuno-affinity for anti-morphine monoclonal antibody was measured using a competitive reaction in which they competed with tritium-labeled morphine. The results obtained are summarized in Table 12.

From the results shown in Table 12, it can be seen that the relative affinity is hardly different for different molecular species, and that the labeling with the fluorochrome hardly changes the reactivity of morphine with the monoclonal antibody.

TABLE 12

| Molecular species | Relative affinity |
|---|---|
| Morphine | 1 |
| Aminomorphine | 1 |
| Tetraazaporphin (Example 1)-PABA-morphine | 0.95 |
| Tetraazaporphin (Example 2)-PABA-morphine | 0.96 |
| Tetraazaporphin (Example 3)-PABA-morphine | 0.94 |
| Tetraazaporphin (Example 4)-PABA-morphine | 0.98 |
| Tetraazaporphin (Example 5)-PABA-morphine | 0.97 |
| Tetraazaporphin (Example 6)-PABA-morphine | 0.97 |
| Tetraazaporphin (Example 7)-PABA-morphine | 0.94 |
| Tetraazaporphin (Example 8)-PABA-morphine | 0.98 |
| Tetraazaporphin (Example 9)-PABA-morphine | 0.96 |

Using the compound of this invention as a fluorochrome for labeling, there can be provided a reagent for fluorescence analysis or a reagent for clinical examination, which is not affected by substances in a living body, such as hemes present in blood, and is useful for qualitative or quantitative analysis of various antigens, drugs, DNAs, etc. and analysis of the base sequence of DNA which use an inexpensive and compact semiconductor laser (670 to 840 nm).

What is claimed is:

1. A water-soluble tetraazaporphin represented by the formula:

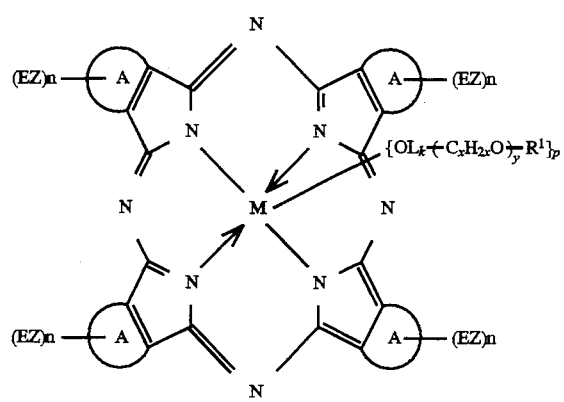

wherein M is Al, Si, P, Ga, Ge or Sc; k is zero or an integer of 1; in the case of k being 1, L is —Si(CH$_3$)$_2$(CH$_2$)$_a$NH—,
—Si(CH$_3$)$_2$(CH$_2$)$_b$NH.COO—,
—Si(CH$_3$)$_2$O— or
—Si(CH$_3$)$_2$NH—;

a and b are independently an integer of 1 to 6; x is an integer of 1 to 6; y is an integer of 1 to 200; $R^1$ is a linear, branched or cyclic alkyl group, an aryl group, a heterocyclic group or an aralkyl group; p is an integer of 1 or 2 indicating the number of groups represented by the formula —OL$_k$—(C$_x$H$_{2x}$O)$_y$—$R^1$ which is bonded to M; four A's, which may be the same or different, are independently a fused polycyclic aromatic ring formed from two or more aromatic rings, which may have substituents XQ's or Q's in a number of m (X is an oxygen atom, a sulfur atom, a nitrogen atom, a phosphorus atom, a silicon atom, a selenium atom, NH.CO, NH.PO$_2$, NH.SO$_2$, O.CO, O.SO$_2$, O.PO$_2$, S.CO, S.SO$_2$, S.PO$_2$, CO, SO$_2$ or PO$_2$; Q is a saturated or unsaturated hydrocarbon group or a heterocyclic group; and each m is the same or different and independently an integer of 1 to 4; each n is the same or different and independently zero or an integer of 1 or more, 4n (the sum of four n's, namely, the total number of EZ's) being an integer of 1 or more; each substituent (EZ) in a number of n is the same or different and independently bonded to the fused polycyclic aromatic ring A and/or Q; and E is a cationic group in the case of Z being an anion, E is an anionic group in the case of Z being a cation, and E is a bonded group containing a polyethylene glycol residue, a polyether residue, a polyamine residue, a polyalcohol residue or a polycarboxylic acid residue in the case of Z being absent.

2. A fluorochrome for labeling comprising the water-soluble tetraazaporphin of claim 1.

3. A reagent comprising the fluorochrome for labeling of claim 2.

4. A reagent comprising the fluorochrome for labeling of claim 2 and a nonionic surfactant.

5. A substance derived from an organism which has been labeled with the fluorochrome for labeling of claim 2.

6. A reagent comprising the labeled substance derived from an organism of claim 5.

7. A reagent comprising the labeled substance derived from an organism of claim 5 and a nonionic surfactant.

8. A reagent according to claim 6, wherein the substance derived from an organism is an antigen, an antibody or a nucleotide.

9. A reagent according to claim 8, wherein the antigen is a drug.

10. A reagent according to claim 8, wherein the antibody is a monoclonal antibody.

11. A reagent according to claim 8, wherein the nucleotide is an oligonucleotide or a polynucleotide.

12. A reagent according to claim 8, wherein the nucleotide is ATP, CTP, GTP, TTP, UTP, dATP, dCTP, dGTP, dTTP, dUTP, ddATP, ddCTP, ddGTP, ddTTP, ddUTP, or a derivative thereof.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 16 base pairs (B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

GTTTCCCAGT CACGAC  16

(2) INFORMATION FOR SEQ ID NO:2:

(i) SEQUENCE CHARACTERISTICS:
   (A) LENGTH: 20 base pairs
   (B) TYPE: nucleic acid
   (C) STRANDEDNESS: single
   (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:2:

ACACAACTGT GTTCACTAGC  20

(2) INFORMATION FOR SEQ ID NO:3:

(i) SEQUENCE CHARACTERISTICS:
   (A) LENGTH: 20 base pairs
   (B) TYPE: nucleic acid
   (C) STRANDEDNESS: single
   (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

CAACTTCATC CACGTTCACC  20